US005476839A

United States Patent [19]
Scott et al.

[11] Patent Number: 5,476,839
[45] Date of Patent: Dec. 19, 1995

[54] BASOPHIL GRANULE PROTEINS

[75] Inventors: Randy W. Scott, Cupertino, Calif.; Gerald J. Gleich, Rochester, Minn.; Craig G. Wilde, Foster City, Calif.

[73] Assignees: Incyte Pharmaceuticals, Inc., Palo Alto, Calif.; Mayo Foundation for Medical Education and Research, Rochester, Minn.

[21] Appl. No.: 245,853

[22] Filed: May 19, 1994

Related U.S. Application Data

[63] Continuation of Ser. No. 943,813, Sep. 11, 1992, abandoned, which is a continuation-in-part of Ser. No. 551,263, Jul. 16, 1990, abandoned.

[51] Int. Cl.$^6$ ............................. A61K 38/02; C07K 2/00
[52] U.S. Cl. ................................. 514/12; 514/2; 514/13; 514/14; 530/300; 530/350; 530/324; 530/325; 530/326; 530/327; 530/328; 530/329; 530/829; 530/837; 530/838
[58] Field of Search ..................................... 530/324, 325, 530/326, 327, 328, 329, 300, 350, 351, 395, 829, 837, 838; 435/199, 212, 814; 514/2, 12, 13, 14

[56] References Cited

U.S. PATENT DOCUMENTS

| | | | |
|---|---|---|---|
| 4,833,092 | 5/1989 | Geysen | 436/501 |
| 4,935,370 | 6/1990 | Franke | 435/252.33 |

OTHER PUBLICATIONS

Denburg et al., "Heterogeneity of Human Peripheral Blood Eosinophil–Type Colonies: Evidence for a Common Basophil–Eosinophil Progenitor," *Blood* (1985) 66(2):312–318.
Stockinger et al., "Human Blood Basophils synthesize Interleukin-2 Binding Sites," *Blood* (1990) 75(9): 1820–1826.
Dvorak et al., "Isolation of the Cytoplasmic Granules of Guinea Pig Basophilic Leukocytes: Identification of Esterase and Protease Activities," *J. Immuno.* (1977) 119(1):38–46.
Denburg et al., "Partial Separation and Functional Characterization of Guinea Pig Basophil–Stimulating Factor," *Int. Arch. Allergy Appl. Immunol.* (1986) 79(3):312–319.
Weller et al., "Biochemical Characterization of Human Eosinophil Charcot–Leyden Crystal Protein (Lysophospholipase)," *J. Bio. Chem.* (1984) 259:15100–15105.
Durack et al., "Purification of human eosinophil–derived neurotoxin," *Proc. Natl. Acad. Sci.* (1981) 78:5165–5169.
Dvorak et al., "Ultrastructural Localization of the Charcot–Leyden Crystal Protein (Lysophospholipase) to Granules and Intragranular Crystals in Mature Human Basophils," *Lab. Inv.* (1989) 60:557–567.
Ackerman et al., "Localization of Eosinophil Granule Major Basic Protein in Human Basophils," *J. Exp. Med.* (1983) 158:946–961.
Wasmoen et al., "Biochemical and Amino Acid Sequence Analysis of Human Eosinophil Granule Major Basic Protein," *J. Biol. Chem.* (1988) 263:12559–12561.
Hunkapiller, "PTH Amino Acid Analysis," *Applied Biosystems* (1985) No. 14, pp. 1–27.
Geysen et al., "Use of peptide synthesis to probe viral antigens for epitopes to a resolution of a single amino acid," *Proc. Natl. Acad. Sci.* (USA) (1984) 81:3998–4002.
Bateman et al. (1990) Biochem. Biophys. Res. Comm. 173:1161–1168.
Long et al. (1984) Biochemistry 23:4828–4837.
Daher et al. (1988) Proc. Nat. Acad. Sci., USA 85:7327–7331.
Selsted et al. (1989) J. Biol. Chem. 264: 4003–4007.
Bhandari et al. (1992) Proc. Nat. Acad Sci, USA, 89:1715–1719.
Lerner, R. A. (1984) Adv. Inmmunol 36: 1–44.
Ogilvie et al., "Basophils and eosinophils in three strains of rats and in athymic (nude) rats following infection with the nematodes *Nippostrongylus brasiliensis* or *Trichinella spiralis*", *Immunology* (1980) 39:385–389.
Juhlin et al., "A New Syndrome Characterized by Absence of Eosinophils and Basophils", *The Lancet* (1977) 1:1233–1235.
Schwartz et al., "The Mast Cell and Mediators of Immediate Hypersensitivity", *Immunological Diseases*, Samter et al., (Eds.), Little Brown & Co. 4th Ed., pp. 157–201 (1988).
Solley et al., "The Late Phase of the Immediate Wheal and Flare Skin Reaction", *The Journal of Clinical Investigation* (1976) 58:408–420.
Charlesworth et al., "Cutaneous Late–Phase Response to Allegen", *J. Clin. Invest.* (1989) 83:1519–1526.
Dvorak et al., "Purification of Basophilic Leukocytes from Guinea Pig Blood and Bone Marrow", *The Journal of Immunology* (1974) 113(6):1694–1702.
Ackerman et al., "Formation of Charcot–Leyden Crystals by Human Basophils", *Journal of Experimental Medicine* (1982) 155:1597–1609.
Castells et al., "Evaluation of Human Peripheral Blood Leukocytes for Mast Cell Tryptase", *The Journal of Immunology* (1987) 138:2184–2189.
Newball et al., "Anaphylactic Release of a Basophil Kallikrein–like Activity", *J. Clin. Invest.* (1979) 64:466–475.
Orenstein et al., "Sulfated Glycosaminoglycans of Guinea Pig Basophilic Leukocytes", *The Journal of Immunology* (1978) 121(12):586–592.

(List continued on next page.)

Primary Examiner—Robert A. Wax
Assistant Examiner—G. E. Bugaisky
Attorney, Agent, or Firm—Karl Bozicevic; Carol L. Francis; Fish & Richardson

[57] ABSTRACT

Several natural polypeptides (basophil granule proteins, "BGP") derived from the cytoplasmic granules of human basophils, and modified forms thereof, are described. These polypeptides, the DNA which encodes them and antibodies which recognize them, are useful as diagnostics for, and treatments for, pathologies involving inflammatory and IgE-mediated responses, parasitic and helminthic infections, hypersensitivity reactions and certain types of leukocytic leukemias.

4 Claims, 12 Drawing Sheets

OTHER PUBLICATIONS

Shoyab, M., et al., "Epithelins 1 and 2: Isolation and characterization of two cysteine–rich growth–modulating proteins" *Proc. Natl. Acad. Sci. USA* (1990) 87:7912–7916.

Galli et al., "Basophils and Mast Cells: Morphologic Insights into their Biology, Secretory Patterns, and Function", *Prog. Allergy* (1984) 34:1–141.

Brown et al., "Ablation of Immunity to *Amblyomma Americanum* by Anti–Basophil Serum: Cooperation Between Basophils and Eosinophils in Expression of Immunity to Ectoparasites (Ticks) in Guinea Pigs", *The Journal of Immunology* (1982) 129(2):790–796.

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Asp  Ile  Gly  Pro  Asp  Gln  His  Thr  Ser  Arg  Pro  Trp  Gly  Gln  Thr
1                    5                        10                       15
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Asp  Val  Lys  Lys  Asp  Met  Glu  Val  Ser  Cys  Pro  Asp  Gly  Tyr  Thr
1                    5                        10                       15
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3
        ( D ) OTHER INFORMATION: /note="X represents an
            unidentified residue."

( i x ) FEATURE:
        ( A ) NAME/KEY: Modified-site
        ( B ) LOCATION: 9
        ( D ) OTHER INFORMATION: /note="X represents an
            unidentified residue."

( i x ) FEATURE:
        ( A ) NAME/KEY: Modified-site
        ( B ) LOCATION: 14
        ( D ) OTHER INFORMATION: /note="X represents an
            unidentified residue."

( x i ) SEQUENCE DESCRIPTION: SEQ ID NO:3:

```
Val  Met  Xaa  Pro  Asp  Ala  Arg  Ser  Xaa  Arg  Pro  Asp  Gly  Xaa  Thr
1                    5                        10                       15
```

( 2 ) INFORMATION FOR SEQ ID NO:4:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 4
        ( D ) OTHER INFORMATION: /note="X represents an
            unidentified residue."

( i x ) FEATURE:
        ( A ) NAME/KEY: Modified-site
        ( B ) LOCATION: 8
        ( D ) OTHER INFORMATION: /note="X represents an unidentified residue."

( i x ) FEATURE:
    ( A ) NAME/KEY: Modified-site
    ( B ) LOCATION: 9
    ( D ) OTHER INFORMATION: /note="X represents an
        unidentified residue."

( x i ) SEQUENCE DESCRIPTION: SEQ ID NO:4:

```
Ala  Ile  Tyr  Xaa  Arg  Ile  Pro  Xaa  Xaa  Ile  Ala  Gly  Glu  Phe  Arg  Tyr
 1              5                        10                       15

Gly  Thr  Val  Tyr  Tyr  Gln  Gly  Ser  Leu
              20                       25
```

( 2 ) INFORMATION FOR SEQ ID NO:5:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 6
        ( D ) OTHER INFORMATION: /note="X represents an
            unidentified residue."

( i x ) FEATURE:
        ( A ) NAME/KEY: Modified-site
        ( B ) LOCATION: 8
        ( D ) OTHER INFORMATION: /note="X represents an
            unidentified residue."

( x i ) SEQUENCE DESCRIPTION: SEQ ID NO:5:

```
Asp  Ile  Pro  Glu  Val  Xaa  Val  Xaa  Leu  Ala  Ala  Asp  Glu  Ser  Leu  Ala
 1              5                        10                       15

Pro  Lys
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Tyr  Pro  Gln  Leu  Ala  Ile  Asn
 1              5
```

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 8
        ( D ) OTHER INFORMATION: /note="X represents an
            unidentified residue."

( x i ) SEQUENCE DESCRIPTION: SEQ ID NO:7:

```
Ser  Ile  Gly  Phe  Val  Glu  Val  Xaa  Leu  Val  Leu
 1              5                        10
```

( 2 ) INFORMATION FOR SEQ ID NO:8:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
Ala  Cys  Tyr  Cys  Arg  Ile  Pro  Ala  Cys  Ile  Ala  Gly  Glu  Arg  Arg  Tyr
1                   5                        10                       15

Thr  Cys  Ile
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Ala  Pro  Ala  Leu  Thr  Ile  Ser  Asn  Gln
1                   5
```

( 2 ) INFORMATION FOR SEQ ID NO:10:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 10
        ( D ) OTHER INFORMATION: /note="This position is X1 which
            is Ser or Arg."

( i x ) FEATURE:
        ( A ) NAME/KEY: Modified-site
        ( B ) LOCATION: 12
        ( D ) OTHER INFORMATION: /note="This position is X2 which
            is Val or Trp."

( i x ) FEATURE:
        ( A ) NAME/KEY: Modified-site
        ( B ) LOCATION: 17
        ( D ) OTHER INFORMATION: /note="X represents an
            unidentified residue."

( i x ) FEATURE:
        ( A ) NAME/KEY: Modified-site
        ( B ) LOCATION: 26
        ( D ) OTHER INFORMATION: /note="X represents an
            unidentified residue."

( x i ) SEQUENCE DESCRIPTION: SEQ ID NO:10:

```
Asp  Ile  Gly  Pro  Asp  Gln  His  Thr  Ser  Xaa  Pro  Xaa  Gly  Gln  Thr  Arg
1                   5                        10                       15

Xaa  Pro  Gln  Leu  Thr  Gly  Gly  Glu  Ala  Xaa  Val
                    20                       25
```

( 2 ) INFORMATION FOR SEQ ID NO:11:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i x ) FEATURE:
   ( A ) NAME/KEY: Modified-site
   ( B ) LOCATION: 7
   ( D ) OTHER INFORMATION: /note="X represents an unidentified residue."

( i x ) FEATURE:
   ( A ) NAME/KEY: Modified-site
   ( B ) LOCATION: 11
   ( D ) OTHER INFORMATION: /note="X represents an unidentified residue."

( x i ) SEQUENCE DESCRIPTION: SEQ ID NO:11:

Arg Asp Val Pro Pro Asp Xaa Val Val Ser Xaa Pro Ser Ser Asp Thr
1               5                   10                  15

( 2 ) INFORMATION FOR SEQ ID NO:12:

( i ) SEQUENCE CHARACTERISTICS:
      ( A ) LENGTH: 24 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 5
      ( D ) OTHER INFORMATION: /note="X represents an unidentified residue."

( i x ) FEATURE:
      ( A ) NAME/KEY: Modified-site
      ( B ) LOCATION: 11
      ( D ) OTHER INFORMATION: /note="X represents an unidentified residue."

( i x ) FEATURE:
      ( A ) NAME/KEY: Modified-site
      ( B ) LOCATION: 17
      ( D ) OTHER INFORMATION: /note="X represents an unidentified residue."

( i x ) FEATURE:
      ( A ) NAME/KEY: Modified-site
      ( B ) LOCATION: 18
      ( D ) OTHER INFORMATION: /note="X represents an unidentified residue."

( x i ) SEQUENCE DESCRIPTION: SEQ ID NO:12:

Gly Asp Val Lys Xaa Asp Met Glu Val Ser Xaa Pro Asp Gly Tyr Thr
1               5                   10                  15

Xaa Xaa Arg Leu Gln Ser Gly Ala
            20

( 2 ) INFORMATION FOR SEQ ID NO:13:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 4
      ( D ) OTHER INFORMATION: /note="X represents an unidentified residue."

( i x ) FEATURE:
      ( A ) NAME/KEY: Modified-site
      ( B ) LOCATION: 10
      ( D ) OTHER INFORMATION: /note="X represents an unidentified residue."

( i x ) FEATURE:
    ( A ) NAME/KEY: Modified-site
    ( B ) LOCATION: 16
    ( D ) OTHER INFORMATION: /note="X represents an unidentified residue."

( i x ) FEATURE:
    ( A ) NAME/KEY: Modified-site
    ( B ) LOCATION: 17
    ( D ) OTHER INFORMATION: /note="X represents an unidentified residue."

( x i ) SEQUENCE DESCRIPTION: SEQ ID NO:13:

```
Asp Val Lys Xaa Asp Met Glu Val Ser Xaa Pro Asp Gly Tyr Thr Xaa
1               5                   10                  15
Xaa Arg Leu Gln Ser Gly Ala
            20
```

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

```
Gly Pro Pro Thr Phe Asn Lys Ile Thr Pro Asn Asp Ala Asp Phe
1               5                   10                  15
```

( 2 ) INFORMATION FOR SEQ ID NO:15:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i x ) FEATURE:
    ( A ) NAME/KEY: Modified-site
    ( B ) LOCATION: 6
    ( D ) OTHER INFORMATION: /note="This position is X3 which is Leu or Asp."

( i x ) FEATURE:
    ( A ) NAME/KEY: Modified-site
    ( B ) LOCATION: 10
    ( D ) OTHER INFORMATION: /note="This position is X4 which is Met or Glu."

( i x ) FEATURE:
    ( A ) NAME/KEY: Modified-site
    ( B ) LOCATION: 11
    ( D ) OTHER INFORMATION: /note="This position is X5 which is Lys, Ile, or Cys."

( i x ) FEATURE:
    ( A ) NAME/KEY: Modified-site
    ( B ) LOCATION: 13
    ( D ) OTHER INFORMATION: /note="This position is X6 which is Pro or Leu."

( x i ) SEQUENCE DESCRIPTION: SEQ ID NO:15:

```
Ala Ile Gln Cys Pro Xaa Ser Gln Phe Xaa Xaa Pro Xaa Phe Leu Ala
1               5                   10                  15
Thr Gly Val Met
            20
```

( 2 ) INFORMATION FOR SEQ ID NO:16:

( i ) SEQUENCE CHARACTERISTICS:

(A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:16:

Asp Ile Pro Glu Val Cys Phe Asn
    1               5

(2) INFORMATION FOR SEQ ID NO:17:

(i) SEQUENCE CHARACTERISTICS:
            (A) LENGTH: 11 amino acids
            (B) TYPE: amino acid
            (C) STRANDEDNESS: single
            (D) TOPOLOGY: linear (xi) SEQUENCE DESCRIPTION: SEQ ID NO:17:

Asp Pro Gly Glu Val Lys Ala Leu Pro Met Gln
    1               5                   10

(2) INFORMATION FOR SEQ ID NO:18:

(i) SEQUENCE CHARACTERISTICS:
            (A) LENGTH: 15 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 8
            (D) OTHER INFORMATION: /note="X represents an
                unidentified residue."

(ix) FEATURE:
            (A) NAME/KEY: Modified-site
            (B) LOCATION: 11
            (D) OTHER INFORMATION: /note="X represents an
                unidentified residue."

(xi) SEQUENCE DESCRIPTION: SEQ ID NO:18:

Lys Pro Gln Met Phe Thr Ile Xaa Gln Asn Xaa Ala Thr Trp Met
    1               5                   10                  15

(2) INFORMATION FOR SEQ ID NO:19:

(i) SEQUENCE CHARACTERISTICS:
            (A) LENGTH: 16 amino acids
            (B) TYPE: amino acid
            (C) STRANDEDNESS: single
            (D) TOPOLOGY: linear (xi) SEQUENCE DESCRIPTION: SEQ ID NO:19:

Lys Ile Gly Gly Phe Glu Val Thr Asp Val Phe Ala Pro Val Met Ala
    1               5                   10                  15

(2) INFORMATION FOR SEQ ID NO:20:

(i) SEQUENCE CHARACTERISTICS:
            (A) LENGTH: 15 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 6
            (D) OTHER INFORMATION: /note="X represents an
                unidentified residue."

(  i x ) FEATURE:
    ( A ) NAME/KEY: Modified-site
    ( B ) LOCATION: 10
    ( D ) OTHER INFORMATION: /note="X represents an
        unidentified residue."

(  i x ) FEATURE:
    ( A ) NAME/KEY: Modified-site
    ( B ) LOCATION: 14
    ( D ) OTHER INFORMATION: /note="X represents an
        unidentified residue."

( x i ) SEQUENCE DESCRIPTION: SEQ ID NO:20:

Ile  Leu  Gly  Val  Phe  Xaa  Val  Glu  Gln  Xaa  Phe  Ser  Phe  Xaa  Leu
1                  5                        10                       15

( 2 ) INFORMATION FOR SEQ ID NO:21:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( x i ) SEQUENCE DESCRIPTION: SEQ ID NO:21:

Asp  Pro  Pro  Thr  Phe  Asn  Lys  Ile  Thr  Pro  Asn  Leu  Leu  Glu  Phe  Ala
1                  5                        10                            15

Asp  Gly  Leu  Tyr  Lys  Gln  Glu
                20

( 2 ) INFORMATION FOR SEQ ID NO:22:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:22:

Ser  Glu  Leu  Thr  Lys  Met  Asn  Gln  Arg  Ser  Phe
1                  5                        10

( 2 ) INFORMATION FOR SEQ ID NO:23:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 8
        ( D ) OTHER INFORMATION: /note="X represents an
            unidentified residue."

( i x ) FEATURE:
        ( A ) NAME/KEY: Modified-site
        ( B ) LOCATION: 11
        ( D ) OTHER INFORMATION: /note="X represents an
            unidentified residue."

( x i ) SEQUENCE DESCRIPTION: SEQ ID NO:23:

Lys  Pro  Gln  Met  Phe  Thr  Ile  Xaa  Gln  Asn  Xaa  Ala  Thr  Trp  Met
1                  5                        10                       15

BASOPHIL GRANULE PROTEINS

CROSS-REFERENCE TO RELATED APPLICATION

This is a continuation of application Ser. No. 07/943,813, filed Sep. 11, 1992, now abandoned which is a continuation-in-part of now abandoned U.S. application Ser. No. 07/551,263, filed Jul. 10, 1990, which is hereby incorporated by reference in its entirety and to which application we claim priority under 35 USC §120.

TECHNICAL FIELD

This invention is related to novel proteins, pharmaceutical compositions containing such, therapeutics and human immunology. More specifically, it relates to proteins found in the cytoplasmic granules of human basophils, to the genes which encode them, to the antibodies which recognize them, and to the use of these proteins, oligonucleotides, and antibodies in the diagnosis and treatment of disease.

BACKGROUND ART

The basophil, along with the mast cell, contains cytoplasmic granules with an affinity for basic dyes. The basophil is produced by the bone marrow and circulates in the blood. Basophils are associated with helminthic parasitic infections and allergic reactions and they possess a high affinity receptor for IgE antibodies. Little is known however about the proteins which comprise the granule, in part because, under normal conditions, basophils constitute less than 1% of peripheral blood cells and it is therefore difficult to obtain an adequate amount of purified material for study.

While some researchers have proposed that basophils are the precursors of mast cells, recent data suggests that basophils represent terminally differentiated leukocytes, possibly more closely related to eosinophils (Galli, S. J. and Lichtenstein, L. M., in *Allergy:Principles and Practice,* Middleton et al (Eds.), 3rd Ed, Vol. 1 (1988), pp 106–134).

Basophils appear to participate in many inflammatory, immunological and pathological reactions. For a general review see Galli et al, *Prog Allergy* (1984) 34:1. The most striking tissue infiltrates of basophils occur in cutaneous basophil hypersensitivity reactions (Galli and Askenase, in *The Reticuloendothelial System:A Comprehensive Treatise,* Abramoff et al (Eds.) pg 321, Plenum Press 1986). Recent studies suggest that basophils are essential for expression of immunity to the feeding of larval *Amblyomma americanum* ticks. Here, basophils may collaborate with eosinophils in the expression of immunity by acting to attract eosinophils into tissues where the eosinophils subsequently release toxic cationic proteins (Brown, S. J. et al, *J Immunol* (1982) 129:790). Basophils are also elevated during helminthic infections, suggesting that they might participate in host defense to these parasites (Ogilvie, B. M. et al, *Immunol* (1980) 39:385; Lindor, L. J., *Parasite Immunol* (1983) 4:13; Juhlin, L. and Michaelsson, G., Lancet (1977) ! :1233). Evidence also exists that basophils function in hypersensitivity reaction (Schwartz, L. B. and Austen, K. F. in *Immunological Diseases,* Samter et al (Eds) Little Brown & Co 4th Ed, pg 157 (1988); Mitchell, E. B. *Clin Rev Allergy* (1983) 1:427), and in IgE mediated cutaneous late phase reactions (Solley, G. O. et al, *J Clin Invest* (1976) 58:408; Charlesworth, E. N. et al, *J Clin Invest* (1989) 83:1519).

Studies of human basophil granule proteins have been limited by the difficulty of obtaining sufficient numbers of basophils because they constitute only about 0.5% of the total leukocyte population. Prior studies of proteins isolated from the basophils of guinea pigs repeatedly immunized with sheep blood revealed a mixture of neutral esterases-proteases and both trypsin and chymotrypsin-like serine hydrolases, Dvorak, H. F. et al, *J Immunol* (1974) 113:169; *J Immunol* (1977) 119:38. Studies of the glycosaminoglycans (GAG) of these proteins showed a mixture of GAGs including chondroitin sulfate, dermatin sulfate, and small amounts of heparin sulfate (Orenstein, N. S. et al, *J Immunol* (1978) 121:586).

Several proteins have been localized to the human basophil granule including the eosinophil major basic protein (Ackerman, S. J. et al, *J Exp Med* (1983) 158:946) and the Charcot-Leyden crystal protein (Ackerman, S. J. et al, *J Exp Med* (1982) 155:1597). In addition, mast cell tryptase can be identified in human basophils at about 40 pg/cell, a level roughly 500-fold lower than in human mast cells (Casteils, M. C. et al, *J Immunol* (1987) 138:2184). In addition, bradykinin generating activity has been ascribed to basophils by virtue of the release of this enzyme from peripheral white blood cells by IgE dependent stimulation (Newball, H. H. et al, *J Clin Invest* (1979) 64:466).

The present invention was facilitated by a patient that presented with basophilic leukemia. Leukocyte counts were over $10^5$ cell/µl and contained 78% basophils. On two occasions this patient underwent cytophoresis for removal of leukocytes and a total of $1.5 \times 10^{11}$ basophils were obtained. Examination of the granule proteins of these basophils have revealed a number of novel proteins with unique N-terminal amino acid sequences.

DISCLOSURE OF THE INVENTION

Several newly identified polypeptides (basophil granule proteins, "BGPs") are described which constitute some of the proteins found in the cytoplasmic granules of human basophils. These polypeptides, the DNA which encodes them and antibodies which recognize them, are critical for diagnostics for, and treatments for, pathologies involving inflammatory and IgE-mediated responses, parasitic and helminthic infections, hypersensitivity reactions and certain types of leukocytic leukemias.

One aspect of the invention is directed to BGPs, which include proteins found in the granules of basophils, and fragments, mutations and modifications of these natural proteins which retain their respective BGP biological characteristics. The polypeptides can be recombinantly produced by cells in culture, produced by chemical synthesis or isolated and purified from basophils.

Other aspects of the invention are an expression system comprising DNAs which encode these BGPs; host cells transformed with these expression systems; and methods to produce BGPs which utilize host cells transformed with said expression systems.

Still other aspects include antibodies, both monoclonal and polyclonal, which are specific for BGPs.

Additional aspects include methods of diagnosis and treatment of diseases characterized by abnormal expression or release of BGPs by basophils or other cells, or by genetic abnormalities within genes encoding BGPs. Further aspects include methods of treating diseases by the administration of the BGPs, antibodies, and DNA described herein.

BRIEF DESCRIPTION OF THE DRAWINGS

FIGS. 2-1 to 2-8 include HPLC chromatograms of human basophil granule proteins obtained per Example 2; and FIGS. 3-1 to 3-3 includes HPLC chromatograms of human basophil granule proteins obtained per Example 3.

MODES OF CARRYING OUT THE INVENTION

Figure 1:
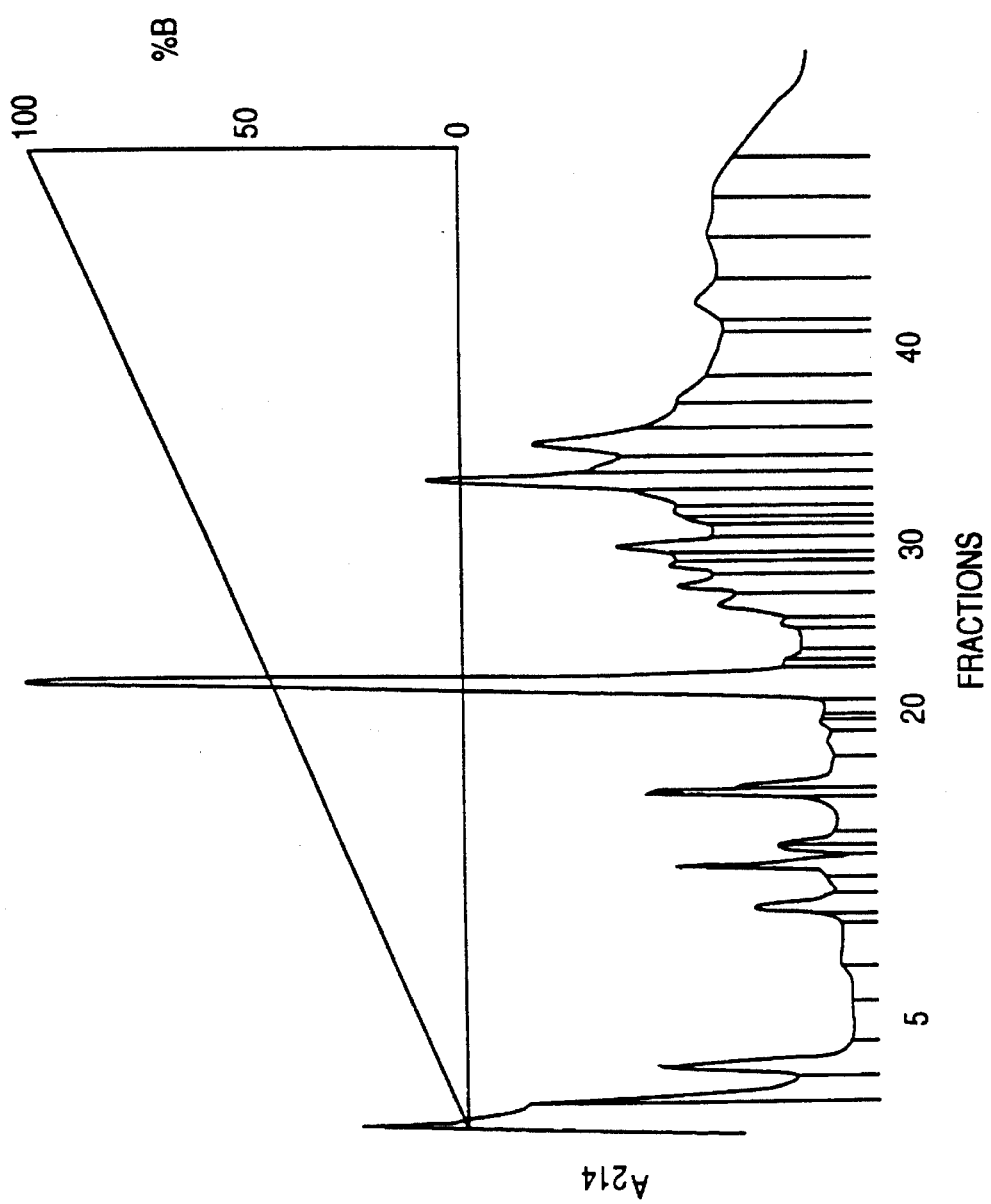
FIG. 1 shows a HPLC chromatogram of human basophil granule proteins obtained per Example 1.
Figure 2A:
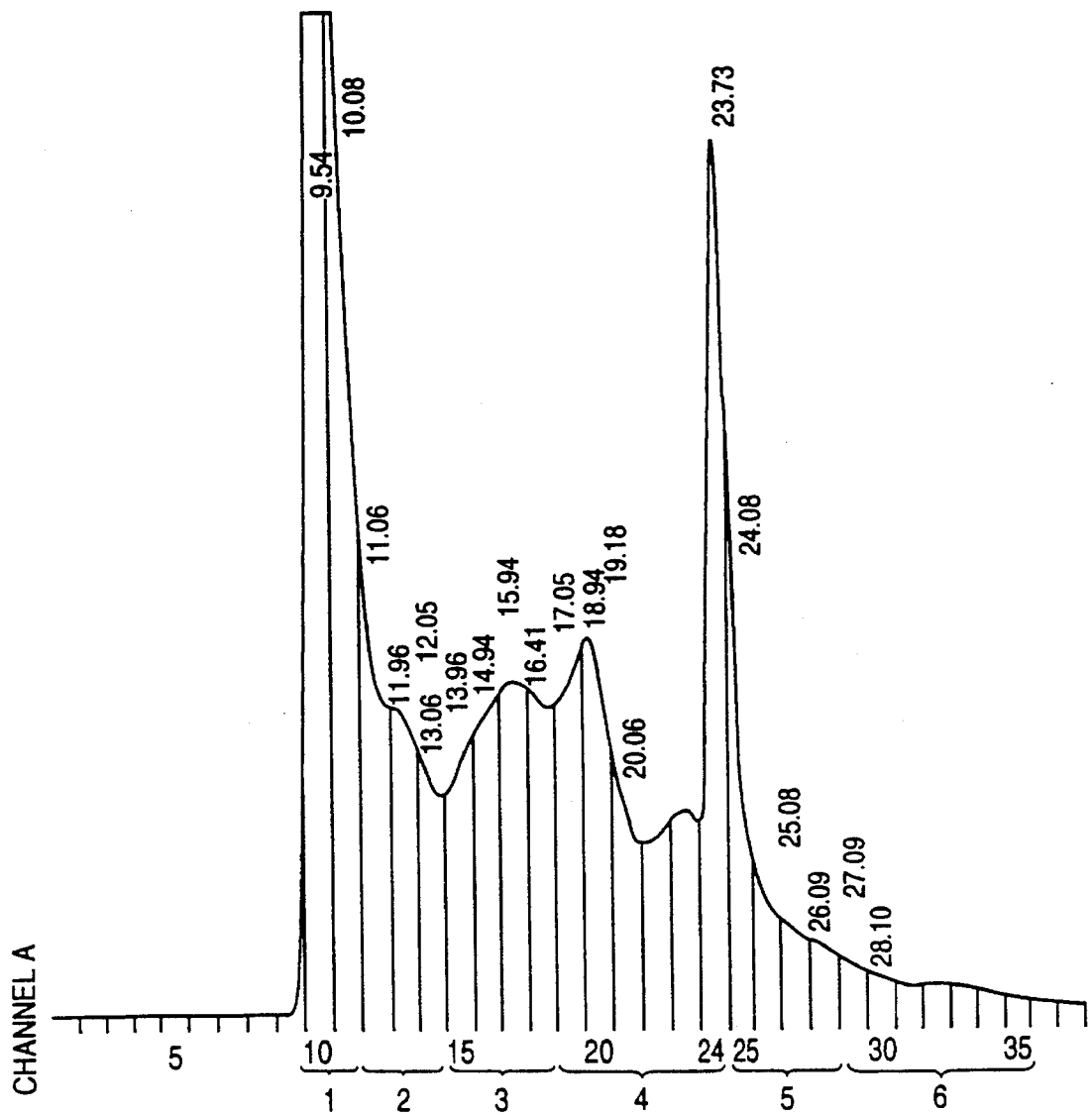
Figure 2B:
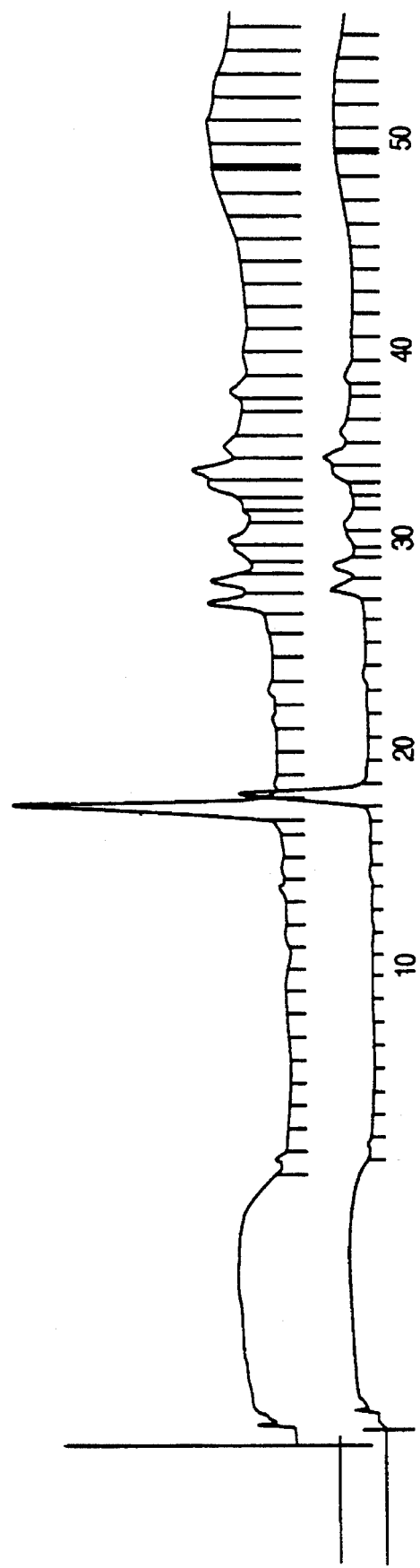
Figure 2C:
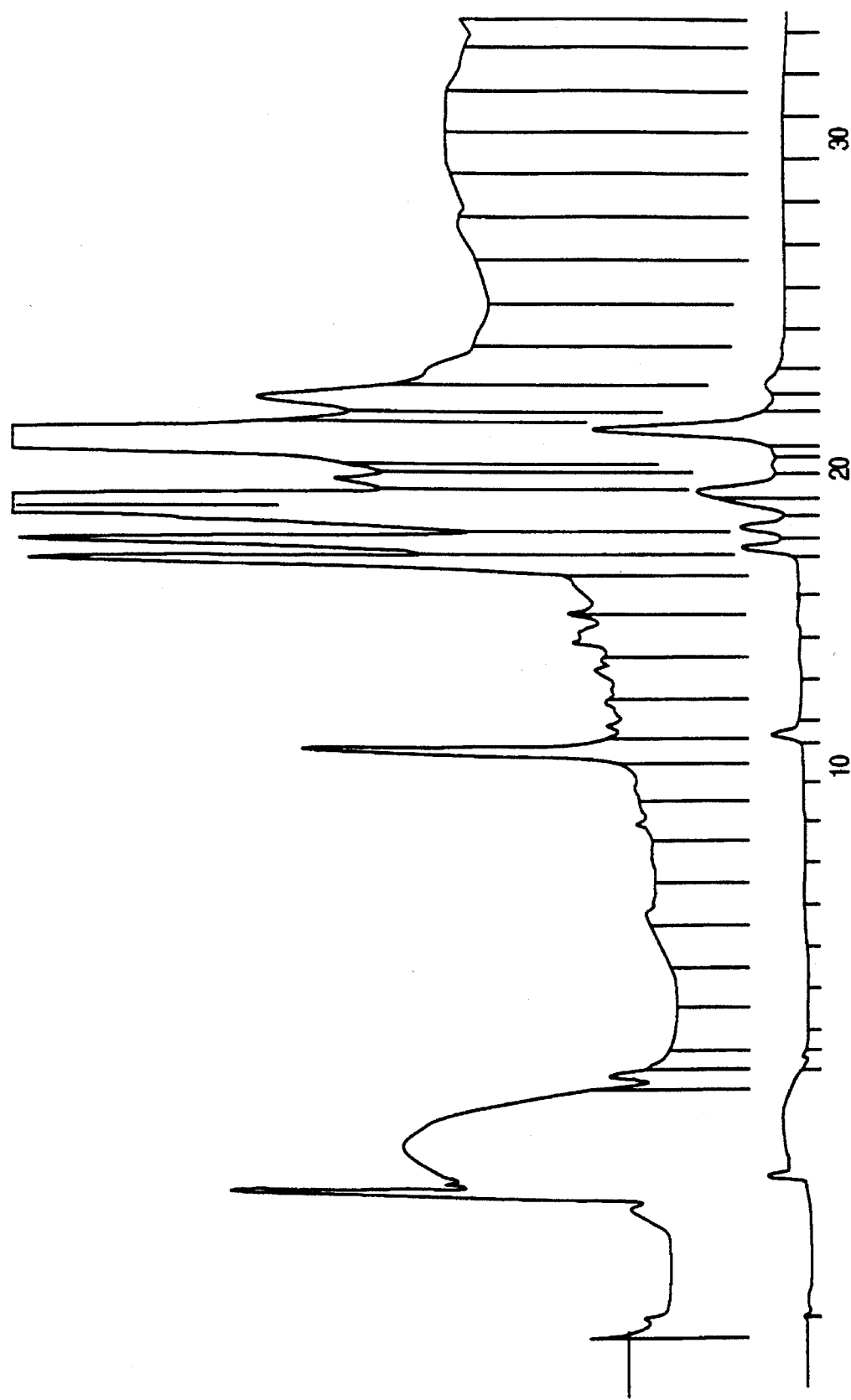
Figure 2D:
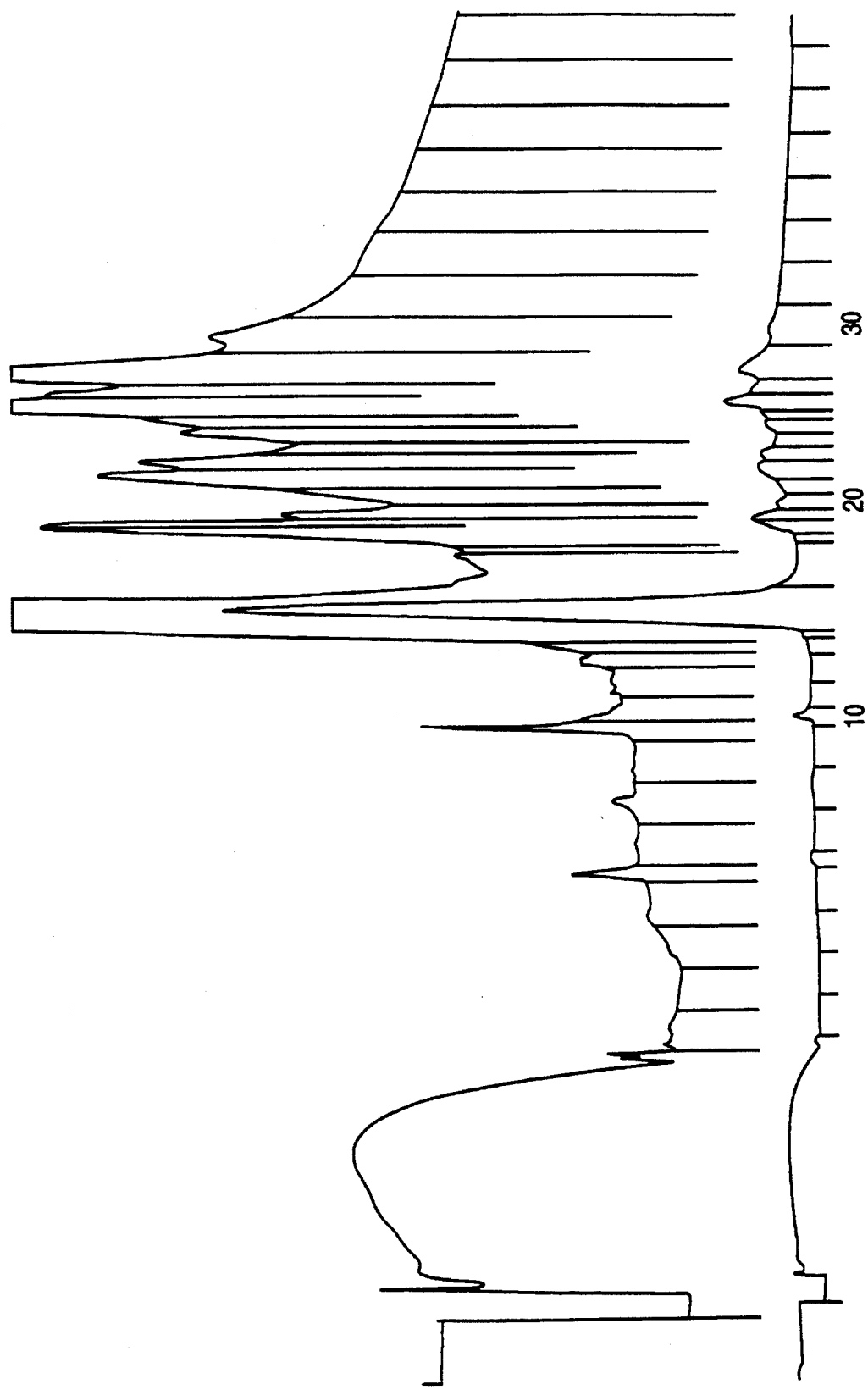
Figure 2E:
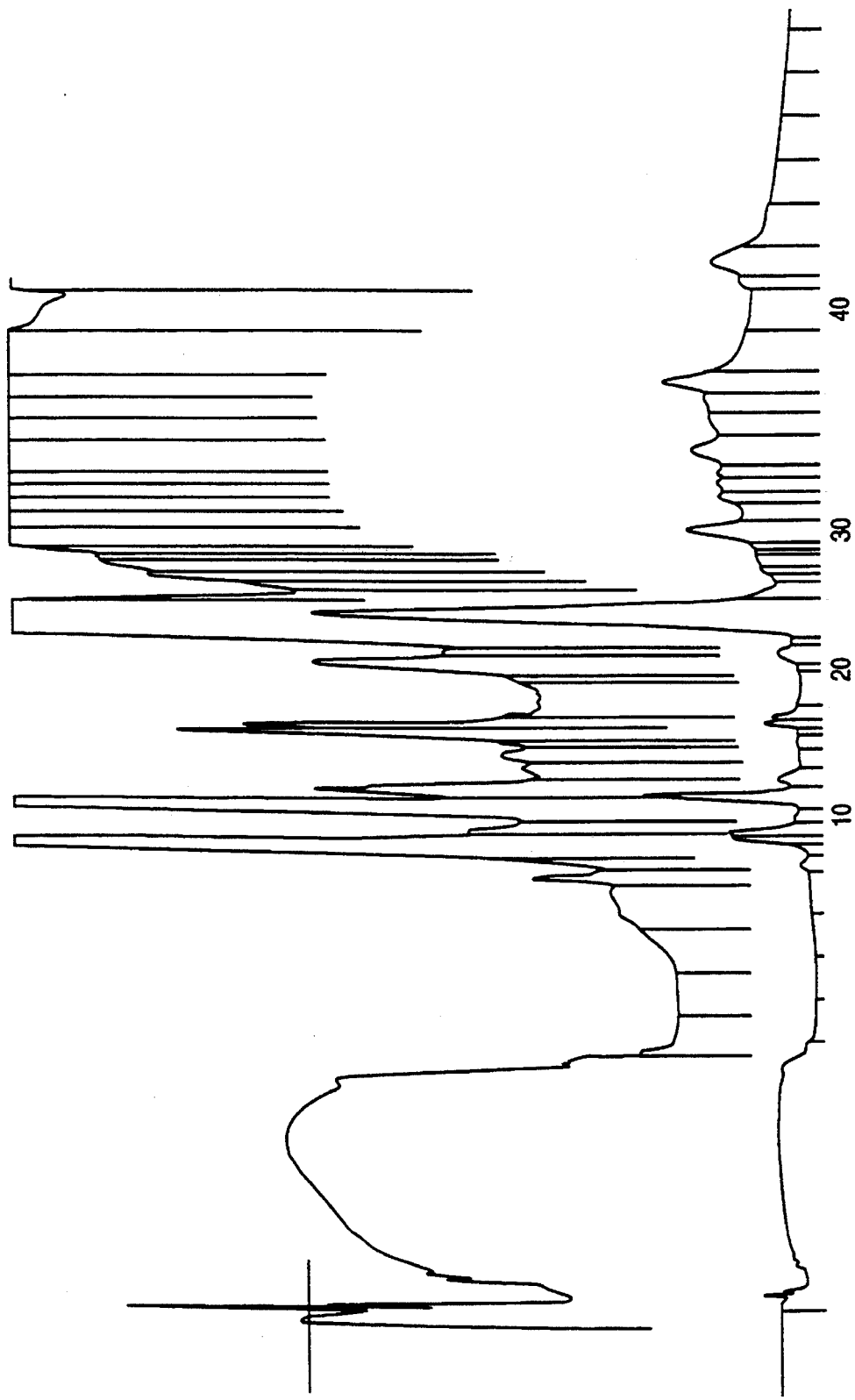
Figure 2F:
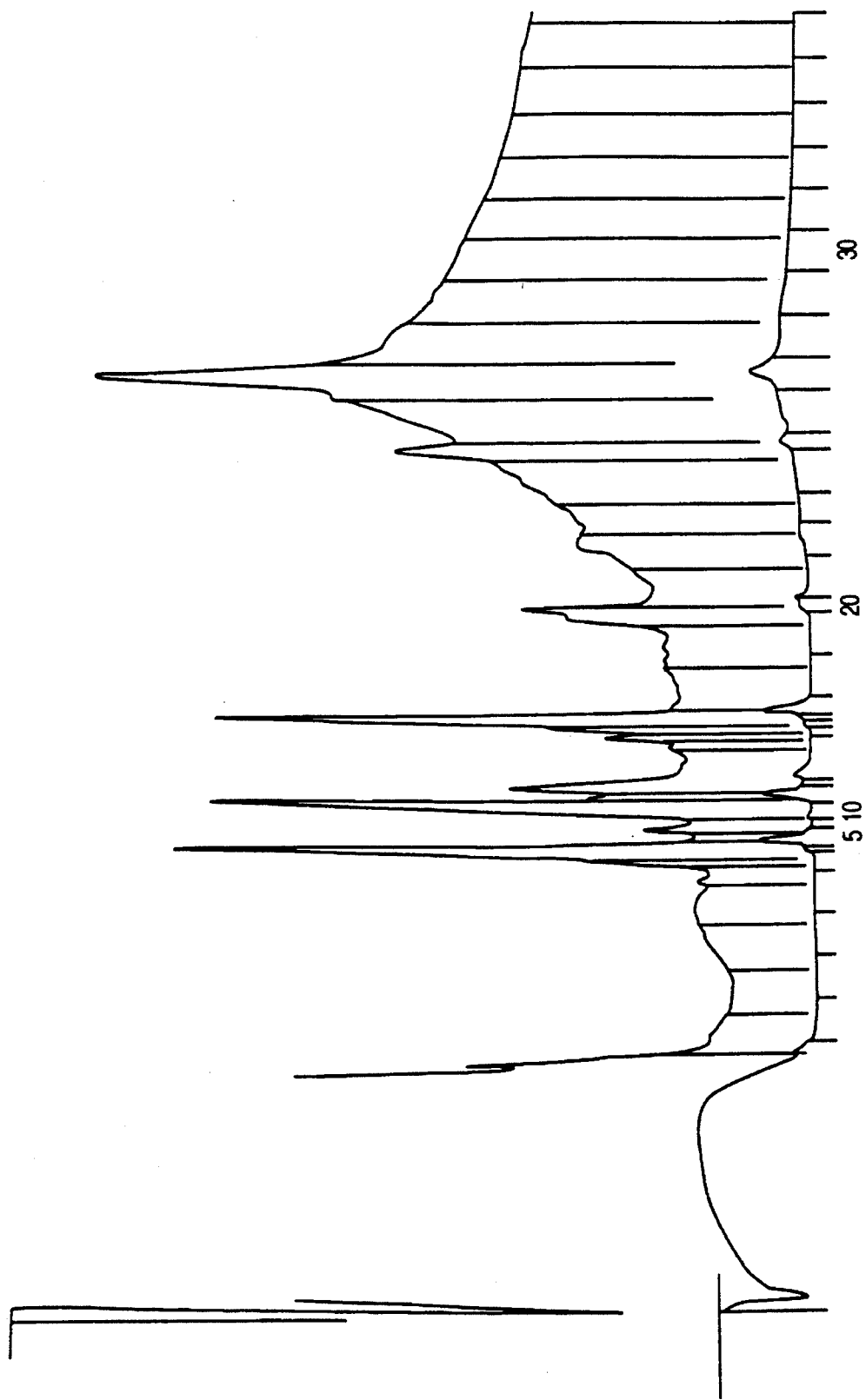
Figure 2G:
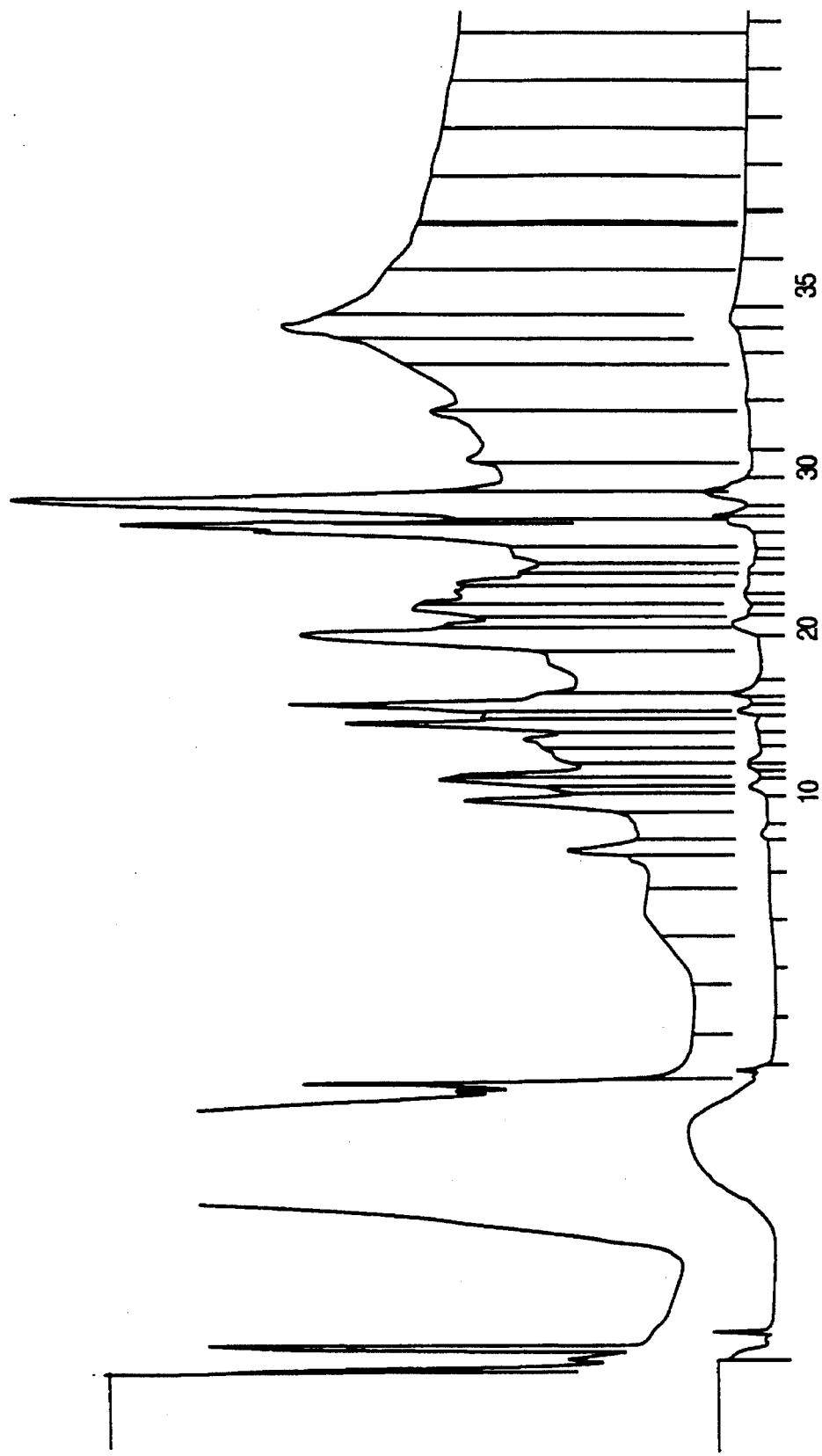
Figure 2H:
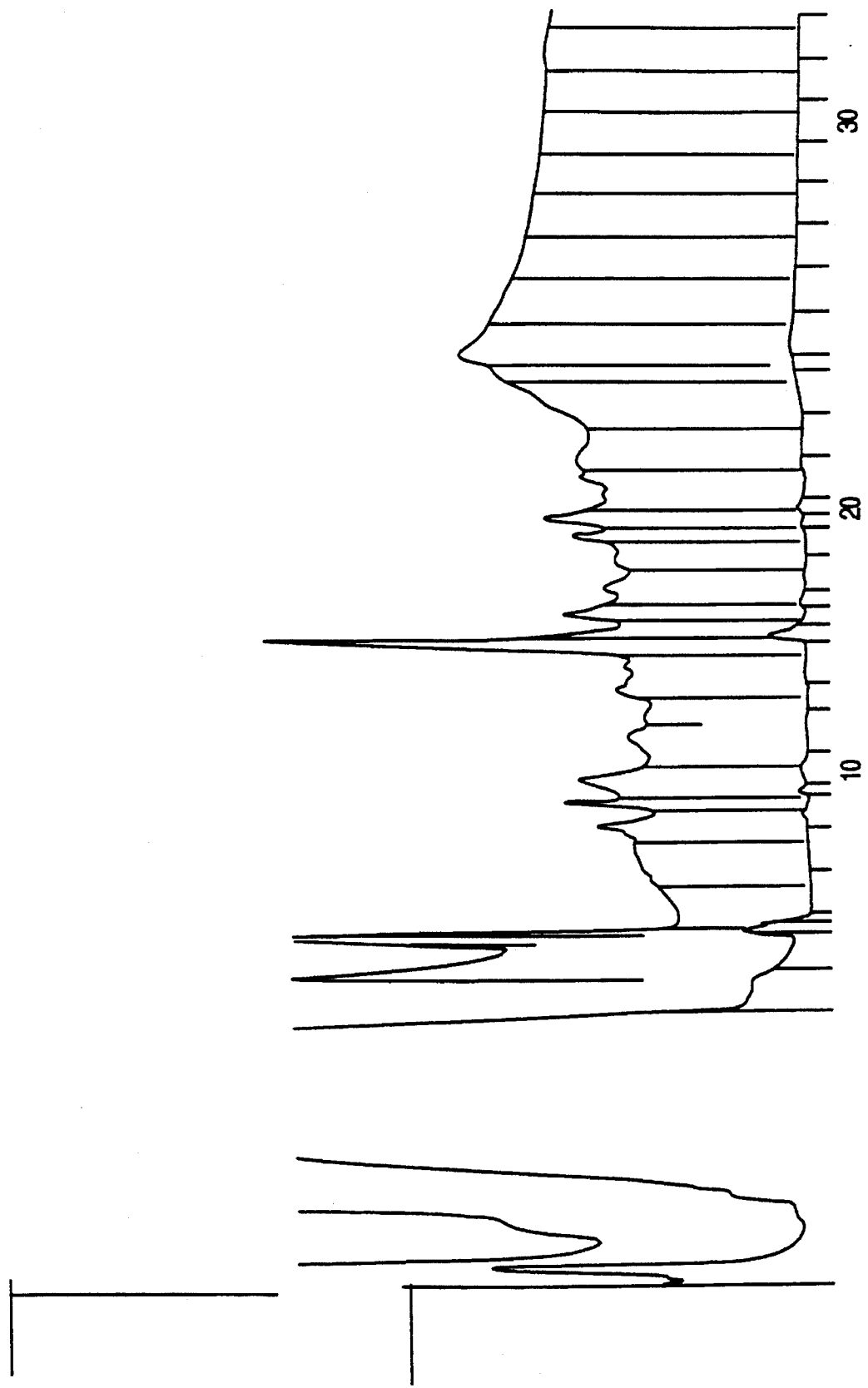
Figure 3A:
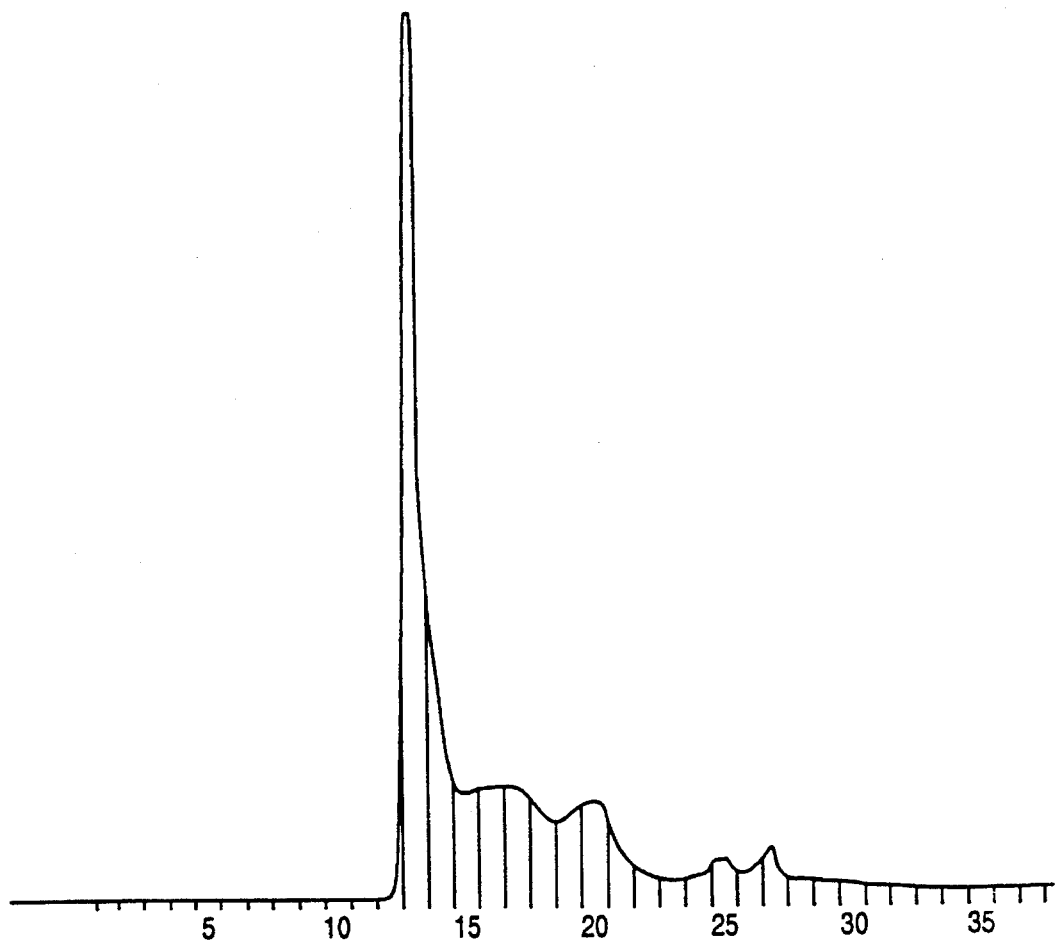
Figure 3B:
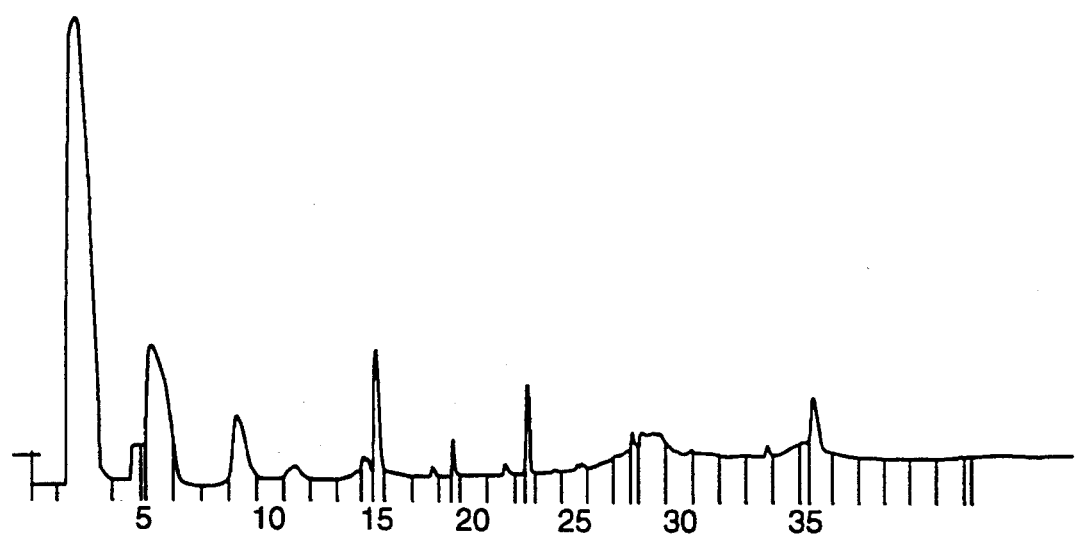
Figure 3C:
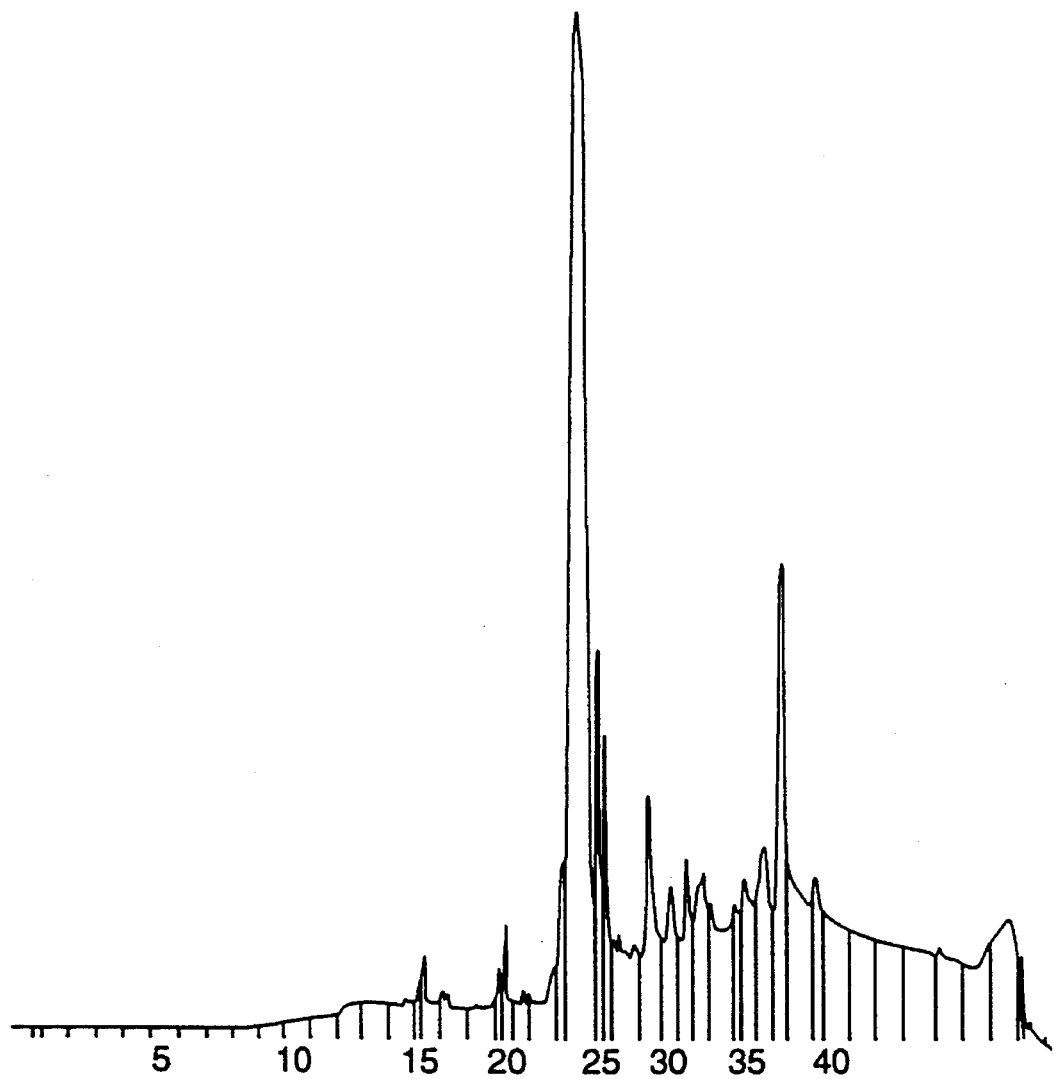

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are described. All publications mentioned herein are incorporated by reference for the purpose of disclosing and describing the specific aspects of the invention to which those publications relate.

As used herein, "basophil granule protein" or "BGP" refers to purified forms of any and/or all of the novel proteins that may be purified from basophil granules as disclosed here as well as fragments and variants thereof, which retain a useful biological characteristic of natural BGP which BGP may be obtained by extraction, synthetically produced or produced using recombinant DNA methodology. It is recognized that basophil granules contain certain proteins that have been demonstrated from other sources. The invention allows the description of additional novel proteins that are discoverable from basophil granules.

A fragment of a BGP is a polypeptide having a primary amino acid sequence identical to any part of a naturally occurring BGP and retaining a useful biological characteristic of the BGP.

A variant of a BGP is any naturally occurring (allelic variant), recombinantly engineered or chemically synthesized peptide or protein resulting from changes in the primary amino acid sequence or posttranslational processing of the BGP described, but retaining useful biological characteristics of the BGP isolated from the cytoplasmic granule of human basophils. The variant forms of natural BGP include those wherein one or more instances of amino acid deletions, substitutions or insertions occur. The variant forms of natural BGP also include those wherein altered patterns of glycosylation or lipidation occur. Variants also include BGP made synthetically wherein substitutions by amino acids which are not encoded by the gene are made. Examples of such amino acids include but are not limited to norleucine, citrulline, ornithine, hydroxyproline, and cysteic acid.

The biological "characteristics" refer to the structural and/or biochemical properties of a BGP and include its specific antigenicity or immunogenicity and its ability to mediate inflammatory and immunological responses in vivo.

A "mutated" protein is a protein with an altered primary structure (relative to the commonly occurring protein) resulting from changes in the nucleotide sequence of the DNA which encodes it. These mutations include allelic variants. A "modified" protein differs from the commonly occurring protein as a result of post-translational events which change the glycosylation or lipidation pattern, or the primary, secondary, or tertiary structure of the protein. Changes in the primary structure of a protein can also result from deletions, additions or substitutions. A "deletion" is defined as a polypeptide in which one or more internal amino acid residues are absent. An "addition" is defined as a polypeptide which has one or more additional internal amino acid residues as compared to the wild type. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred altered forms of "natural" BGP described above are those which have at least 80% homology with natural BGP. At least 90% homology is more preferred, especially those including conservative substitutions.

Homology is calculated by standard methods which involve aligning two sequences to be compared so that maximum matching occurs; and then calculating the percentage of matches. The altered forms of natural BGP include those wherein one or more of the residues of the native sequence is deleted, substituted for, or inserted by a different amino acid or acids.

Preferred substitutions are those which are conservative, i.e., wherein a residue is replaced by another of the same general type. As is well understood, naturally occurring amino acids can be subclassified as acidic, basic, neutral and polar, or neutral and nonpolar. Furthermore, three of the encoded amino acids are aromatic. It is generally preferred that peptides differing from the natural BGP contain substitutions which are from the same group as that of the amino acid replaced. Thus, in general, the basic amino acids Lys, Arg, and His are interchangeable; the acidic amino acids aspartic and glutamic are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable. While proline is a nonpolar neutral amino acid, it presents difficulties because of its effects on conformation, and substitutions by or for proline are not preferred, except when the same or similar conformational results can be obtained. Polar amino acids which represent conservative charge include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. Some substitutions by amino acids from different classes may also be useful to produce altered BGP.

It should further be noted that if the BGP is made synthetically, substitutions by amino acids which cannot be encoded by genes may also be made. Alternative residues include, for example, the omega amino acids of the formula $N_2N(CH_2)_nCOOH$ wherein n is 2–6. These are neutral, nonpolar amino acids, as are sarcosine (Sar, t-butyl alanine (t-BuA), t-butyl glycine (t-BuG), N-methyl Ile (N-MeIle), and norleucine (Nle). Phenyl glycine, for example, can be substituted for Trp, Tyr, or Phe as aromatic neutral amino acids; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be retained if one or more of these is substituted by hydroxyproline (Hyp).

It should be further noted that if the BGP is produced recombinantly as an intracellular protein, an N-terminal methionine residue may be retained in the finished product. Cleavage of the N-terminal methionine to liberate the native sequence may or may not be complete.

The biological "characteristics" of a protein refer to the structural or biochemical function of the protein in the normal biological processes of the organism in which the protein naturally occurs. Examples of biological characteristics of a BGP include its specific antigenicity or immunogenicity, its anti-helminthic activity when this is associated with a particular protein, and/or its ability to mediate inflammatory and immunological responses in vivo.

A host cell "expresses" a gene or DNA when the gene or DNA is transcribed. A protein or polypeptide is "expressed" when the protein or polypeptide has been produced.

"Recombinant host cell" means a procaryotic or eucaryotic cell which contains an expression vector comprising heterologous structural DNA and is capable of expressing the polypeptides encoded by the heterologous DNA.

A. Isolation of Basophil Granules

Clinical hematology laboratories are monitored to identify patients with chronic myelogenous leukemias with greater than $2-3 \times 10^4$ leukocytes/µl of blood and 10– 20% basophils. The basophils are purified by centrifugation over a cushion of Ficoll-Hypaque from which 95% are recovered from the interface with greater than 90% purity.

Purified basophils are lysed using modifications of the procedures described by Dvorak et al, *J Immunol* (1977) 119:38 (supra), for purification of guinea pig basophil granule proteins. Briefly, and in a typical and illustrative procedure, purified basophils are washed with PBS and contaminating erythrocytes are lysed by exposure to Tris-ammonium chloride for 5 minutes. The cell suspension is centrifuged at about 400 g, washed with Hank's BSA-EDTA and suspended in cold 0.25M sucrose containing DNAase and heparin using a volume of 15 ml for $8 \times 10^8$ basophils. The cell suspension is next centrifuged at 400 g for 10 minutes and the sediment is again suspended in 0.25M sucrose containing 2 mg DNAase per 15 ml cell suspension. After 1–2 minutes, heparin (20 IU) dissolved in 2 ml 0.24M sucrose is added and the preparation is subjected to a shearing force by repeated passage (15 times) through a 20 gauge needle. The suspension is centrifuged at 400 g to remove any remaining intact cells, and the granules are then purified by centrifugation through a cushion of 40% sucrose. Finally, the proteins of the isolated basophil granules are solubilized by exposure to 0.05M borate buffer at pH 9 in the presence of 5 mM diisopropylfluorophosphate, $1 \times 10^7$M pepstatin A, and 10 mM EDTA to inhibit protease activity.

B. Protein Fractionation

The solubilized proteins of human basophilic granules, in the same solvent described supra, are separated by reverse phase HPLC using a Brownlee BU-300 C4 column. The mobile phase is 0.1% trifluoroacetic acid (TFA) containing 0–70% acetonitrile. Fractions are collected across the acetonitrile gradient as shown in FIG. 1, where absorbance at 214 nm is shown on the ordinate. The relative homogeneity of each fraction is determined by SDS-PAGE electrophoresis.

Although reverse phase HPLC is an extremely powerful technique, not all human basophil granule proteins can be purified by this technique alone. Thus, size exclusion chromatography can also be employed as a preliminary fractionation (e.g. Bio Sel TSK 125 in 50 mM phosphate pH 6.9) prior to HPLC.

If additional purification of size exclusion chromatography fractions is necessary prior to HPLC, ion exchange chromatography can also be employed. A Mono-Q column (Pharmacia) is used under conditions as would be understood in the art whereby most typical proteins would bind to the column (e.g. 20 mM Tris, pH9.0). The proteins are then eluted in a gradient from 0 to 2M NaCl.

Purified proteins recovered from reverse phase HPLC are sequenced by subjecting up to 100 pmoles (estimated from chromatographic peak height and staining intensity on acrylamide gels) to automated Edman degradation.

For some granule proteins N-terminal sequencing may not be adequate to support efforts to clone the cDNAs. For instance, some granule proteins may be blocked or modified at the N-terminal or alternatively, the N-terminal sequences may not show favorable regions for generation of oligonucleotide probes. Such proteins are digested with trypsin and the tryptic peptides are purified and sequenced in order to generate additional information. The protein is concentrated to a 5 µl volume by vacuum centrifugation, and is then digested by incubation (4 hours, 37° C.) with 1/40 (w:w) TPCK-trypsin in 1 ml of 50 mM ammonium bicarbonate, pH 8.0. Tryptic fragments are purified for sequencing by reverse phase HPLC using a Brownlee RP 18 narrow bore column and an Applied Biosystems 130A liquid chromatograph or other suitable device for HPLC—designed specifically for purification of pmole samples.

Sequence data thus obtained are compared to known protein sequences by computerized searches of the Protein Identification Resource of the NBRF, and/or of the Swiss protein database, in order to determine their novelty or relationship to other protein sequences.

C. Protein Sequencing.

Protein sequencing is performed by automated Edman degradation utilizing a Applied Biosystems 477A Protein Sequenator. Those skilled in the art will recognize that sequence assignments based on a single analysis are subject to a degree of uncertainty. [Hunkapiller, M. W. et al. in *Methods of Protein Microcharacterization* ed. Shively, J. E. (1986) The Humana Press, Clifton, N.J., pp. 223–247; Hunkapiller M. W., *Applied Biosystems Protein* Sequences Users Bulletin #14 (1985)]. Particularly, when assignments at a given cycle are based on analysis of low quantities of the derivatized amino acids, a certain level of error is expected. These errors are most frequently misidentifications of amino acids which are more difficult to identify, namely Ser, Thr, His, Arg and Trp.

Positive identification of Cys is a special problem. Without prior modification of the proteins, Cys is not detectable but its presence may be inferred by the absence of an appropriate signal in that cycle.

Lag is a well known phenomenon in sequencing, where signal deriving from cycle n is also present in cycle n+1. Lag presents a special problem when Cys is present at cycle n+1 since the amino acid present at cycle n may mistakenly be assigned at cycle n+1 due to the lag phenomenon.

Because of such characteristic uncertainties, data from an analysis may support more than one interpretation. Nevertheless, examination of the sequence data allows one skilled in the art to judge whether two sequences derive from the same protein, even when some discrepancies exist.

In accordance with the considerations, the sequences determined are submitted as a description rather than a definition of the proteins which have been isolated.

D. Screening of cDNA Libraries and the Molecular Cloning of Unique Basophil Granule Protein Encoding DNA Basophils mature in cultures of human umbilical cord blood cells. Thus these cultures can be used to prepare a cDNA library which is then screened for particular DNA sequences that encode proteins unique to human basophil granules (BGP) (Saito, H. et al, Proc Nat *Acad Sci* (1988) 85:2288).

Other candidate cDNA libraries which may express BGPs include unstimulated HL-60 cells, or HL-60 cells driven to basophilic differentiation by culturing in a protein free medium (Muroi, K. et al, *Leukemia Res* (1989) 13:157) or in the presence of sodium butyrate (Hutt-Taylor, S. R. et al., *Blood* (1988) 71:209). Although basophils and mast cells appear to be distinct in their lineages, granules of both cells contain mast cell tryptase (Casteils, M. C. et al, *J Immunol* (1987) 138:2184) and these cells may therefore share other common proteins. Therefore cDNA libraries made from human mast cells (e.g. HMC-1) are another source of BGP encoding sequences. The preparation of these cDNA libraries is described in detail in Maniatis, T. et al, *Molecular Cloning*, (1982) CSHL Press, and is well known to those skilled in the art. A convenient approach is the insertion of cDNA fragments into a lambda phage vector e.g. lambda gt10 or lambda gt11 as described by Maniatis, Supra.

Methods of screening cDNA libraries are also well known to those skilled in the art. The amino acid sequence of the BGPs is analyzed for example utilizing programs from DNAstar (Madison, Wis.) in order to identify optimal regions for construction of oligonucleotide probes. Redundant oligonucleotide probes are synthesized with a DNA synthesizer (380A: Applied Biosystems Inc. Foster City, Calif.) by the phosphoramidite method. Oligonucleotides are purified on Sephadex G-50 columns and stored at $-20°$ C. The redundant probes are 5'-labeled with $\tau$-$[^{32}P]$ATP (E.I. du Pont de Nemours & Co., Inc., Boston, Mass.) using T4 polynucleotide kinase. Libraries are screened using up to $10^6$ individual plaques per library, with the redundant oligonucleotide probes. Duplicate nylon membranes containing phage are prepared and prehybridized in 5× SSPE (0.9M Nail, 50 mM $NH_2PO_4$, 5 mM EDTA, pH7.4), 0.2% SDS, and 0.005% denatured salmon sperm DNA for 2 hours at 50° C. with 8 filters per 50 ml prehybridization fluid per bag. Membranes are hybridized with approximately 1 ng of labeled probe per ml, in fresh hybridization fluid, overnight at the appropriate temperature for the redundant probe mixture. Membranes are then washed at room temperature for 45 minutes in 1 liter of 5× SSPE per 40 filters, followed by a 1 minute wash in fresh buffer at 50° C., slightly air-dried, and exposed to Kodak XAR-5 film, with intensifying screens, for 72 hours at $-70°$ C.

After analysis, filters are stripped of hybridized label by incubation in 5× SSPE at 70° C. for 10 minutes and subsequently hybridized with a second probe under the same conditions. This procedure is repeated for each probe. Recombinant clones which hybridize with probes will be selected from the library and plaque purified.

Recombinant phage DNA is then purified and digested with an appropriate restriction endonuclease to yield the amplified cDNA insert. Inserts are then ligated into M13mp series phage and sequenced using the dideoxy method described by Sanger (Biggin, M. D. et al, *Proc Nat Acad Sci* (1983) 80:3963). Depending on the size of the cDNA, it may be necessary to restrict the clone, and subclone the fragments into M13. If the cDNA clones are not complete, a repeat screen of the library with the partial cDNA would be required. The complete sequence of the BGP cDNA is then compared against known sequences in the GenBank database. DNAstar is used for nucleotide and polypeptide analyses and sequence comparisons.

Selected cDNA inserts which encode a BGP can then be incorporated into an expression system. The cDNA is operably linked to heterologous control sequences to form an expression vector. The control sequences are chosen to be functionally compatible with the recombinant host cell into which the expression vector is introduced. These procedures are known to those skilled in the art and described in Maniatis, supra.

Expression can be in procaryotic or eucaryotic systems. Procaryotes most frequently are represented by various strains of *E. coli*. However, other microbial strains may also be used, such as bacilli (e.g. *Bacillus subtilis*), various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., *Gene* (1977) 2:95. Commonly used procaryotic control sequences, which are defined herein to include operons with promoters for transcriptional initiation, optionally with an operator, along with ribosome binding site sequences, include such commonly used promoters as the beta-lactamase (penicillinase) promoter, lactose (lac) promoter systems (Chang et al., *Nature* (1977) 198:1056), the tryptophan (trp) promoter system (Goeddel et al., *Nucleic Acids Res* (1980) 8:4057), the lambda-derived PL promoter and N-gene ribosome binding site (Shimatake et al., *Nature* (1981) 292:128). Any available promoter system compatible with procaryotes can be used.

The expression systems useful in eucaryotic hosts comprise promoters derived from appropriate eucaryotic genes. A class of promoters useful in yeast, for example, includes promoters for synthesis of glycolytic enzymes, including those for 3-phosphoglycerate kinase (Hitzeman et al., *J Biol Chem* (1980) 255:207). Other promoters include those from the enolase gene (Holland, M. J., et al. *J Biol Chem* (1981) 256:1385) or the Leu2 gene obtained from YEp13 (Broach,, J., et al., *Gene* (1978) 8:121).

Suitable mammalian promoters include metallothionein, the early and late promoters from SV40 (Fiers et al., *Nature* (1978) 273.:113), or other viral promoters such as those derived from polyoma, adenovirus II, bovine papilloma virus or retroviruses. Suitable viral and mammalian enhancers may also be used. In the event plant cells are used as an expression system, the nopaline synthesis promoter is appropriate (Depicker, A., et al., *J Mol Appl Gen* (1982) 1:561).

The expression system is constructed from the foregoing control elements which are operably linked to the BGP sequences by employing standard ligation and restriction techniques which are well understood in the art. Isolated plasmids, DNA sequences, or synthesized oligonucleotides are cleaved, tailored, and relegated in the forms desired.

E. Production of Antisense and Triple Helix Oligonucleotides

Antisense oligonucleotides can be designed and produced based upon the nucleotide sequence of cDNA encoding a BGP. The antisense oligonucleotide can be designed and used to regulate the translation within the cell of the specific mRNA to which it is complementary according to methods known in the art (Green et al., *Ann Rev Biochem* (1986) 55:569; Rossi et al., *Pharmacol Ther* (1991) 50:245).

The antisense reagent is made complementary to some portion of the mRNA encoding the BGP, preferably including a portion of the mRNA at or near the translation initiation site in the 5' region. In one approach, the antisense reagent may be RNA or preferably a modified RNA wherein the sugar phosphate backbone has been modified to increase resistance to RNase activity or otherwise improve pharmacokinetic or pharmacodynamic properties. In another approach the antisense oligonucleotide may be a DNA, which has been ligated to a promoter in an antisense orientation, such that transcription of the DNA produces a mRNA complementary to the mRNA encoding a BGP. The antisense DNA may be incorporated into an expression vector for introduction into the body.

Triple helix oligonucleotides can also be designed and produced based upon the nucleotide sequence of cDNA encoding a BGP. The triple helix oligonucleotide can be used to regulate the transcription within the cell of the specific DNA to which it is targeted and particularly to inhibit expression of a specific gene in individuals having diseases associated with expression of the gene. Homopurine and homopyrimidine sequences which are appropriate for triple helix formation can be designed by methods known in the art (Griffen et al. *Science* (1989) 245:967). The effectiveness of triple helix oligonucleotide can be improved by synthesizing the reagents using the unnatural α-anomeric nucleotides to improve their nuclease resistance properties or by derivitizing the oligonucleotides with an intercalating agent such as ethidium bromide to stabilize the triple helix, once it has been formed.

Antisense molecules are introduced into the body in one method by injecting the oligonucleotide either alone, encapsulated in a liposome or incorporated into a viral particle.

F. Analysis of the Genomic Sequence of BGP DNA

BGP-encoding genes are obtained from the genomic library of human fetal liver DNA in Charon 4A phage (ATCC 37333). The library contains $10^6$ independent recombinants with an insert size of 15–20 kb and it is screened with cDNA essentially as previously described. Phage are sequentially adsorbed onto duplicate 8×8 cm nylon membrane filters. Filters are prehybridized in 5× SSPE, 50% formamide, 5× Denhardt's solution, 0.5% SDS and 0.005% denatured salmon sperm DNA for 2 hours at 42° C. with 8 filters per 50 ml of prehybridization fluid. Filters are hybridized with approximately 1.0 ng of labeled basophil protein cDNA per ml of fresh prehybridization fluid, containing 10% dextran sulphate and 2× Denhardt's solution, overnight at 42° C. BGP cDNA is labeled with $\alpha^{32}P$ dCTP and purified by Sephadex G-50 chromatography. Filters are then washed twice at room temperature for 15 minutes in 1 liter 2× SSPE and 0.2% SDS per 40 filters, followed by two 15 minute 50° C. washes in 0.1× SSPE and 0.2% SDS, slightly air-dried, and exposed to Kodak XAR-5 film, with intensifying screens, for 48 hours at −70° C.

Positive clones are selected from the library and plaque purified. Various probes derived from the cDNA are utilized to determine whether or not a complete copy of the gene is contained within the genomic clone. Recombinant phage DNA is next extracted, purified, and subjected to restriction digestion—all processes which are well known to those skilled in the art. Southern blots of the restriction fragments are hybridized with BGP cDNA to identify fragments containing the BGP gene. These fragments are then isolated and sequenced. From this information a restriction map is constructed and the introns of the gene are identified.

G. Preparation of Antibodies to BGPs

Two approaches are utilized to raise antibodies to BGP and both approaches can be used to generate either polyclonal or monoclonal antibodies. In one approach, as denatured protein from the reverse phase HPLC separation is obtained in quantities up to 75 μg, this denatured protein can be used to immunize mice using standard protocols; about 25 μg is adequate for immunization. For screening hybridomas, the denatured protein, which is soluble in 0.1% TFA and acetonitrile, can be radioiodinated and used to screen murine B-cell hybridomas for those which produce antibody. This procedure requires only small quantities of protein such that 20μg would be sufficient for labeling and screening of several thousand clones.

In the second approach, the amino acid sequence of BGPs as deduced from the gene is analyzed to determine regions of high immunogenicity. The corresponding polypeptides are synthesized and are used in suitable immunization protocols to raise antibodies. Analysis to select appropriate epitopes is described by, for example, Ausubel, F. M. et al, in *Current Protocols in Molecular Biology*, John Wiley & Sons, Vol. 2, Sec. IV, pp 11.14.1, 1989). The optimal selections are usually the C terminus, the N terminus and internal regions of the polypeptide, which are likely to be exposed to the external environment when the protein is in its natural conformation (this determination is based on the hydrophilicity of the sites). Typically, selected peptides, about 15 residues in length, are synthesized using an Applied Biosystems Peptide Synthesizer Model 431A using fmoc-chemistry and coupled to keyhole limpet hemocyanin (KLH; Sigma) by reaction with m-maleimidobenzoyl-N-hydroxysuccinimide ester (MBS) (See Ausubel et al, supra at pp 11.15.1). A cysteine is introduced at the N-terminus of the peptide to permit coupling to KLH. Rabbits are immunized with the peptide-KLH complex in complete Freund's adjuvant and the resulting antisera tested for antipeptide activity, for example, by binding the peptide to plastic, blocking with 0.1% BSA, reacting with antisera, washing and reacting with radioiodinated affinity purified specific goat antirabbit IgG.

Hybridomas may be also be prepared and screened using standard techniques. Hybrids are screened using radioiodinated BGP to identify those producing monoclonal antibody. In a typical protocol, prongs of plates (FAST, Becton-Dickinson, Palo Alto, Calif.), are coated with affinity purified specific rabbit-antimouse (or suitable anti species Ig) antibodies at 10 μg/ml. The coated prongs are blocked with 0.1% BSA, washed and exposed to supernatants from hybridomas. After incubation the prongs are exposed to radiolabeled protein, 1 ng/ml. Clones producing antibodies will bind a quantity of radioactivity which is detectable above background. Such clones are expanded and subjected to 2 cycles of cloning at 0.3 cell/well. Cloned hybridomas are injected into pristine treated mice to produce ascites, and monoclonal antibody is purified from the ascitic fluid by affinity chromatography on protein A.

H. Use of Anti-BGPs in Diagnosis

Anti-BGPs are useful for the diagnosis of prepathologic conditions and as well as chronic and acute diseases which are characterized by abnormalities in the amount or distribution of BGPs. For example, the BGPs disclosed herein can be used to generate polyclonal and preferably monoclonal antibodies. These antibodies can be used to detect the BGPs in a sample such as a blood sample and determine the presence of and level of the BGPs in the sample. The type and/or amount of BGPs detected can be compared to a known standard—an average for healthy individuals. Readings outside of the standard would be useful information in diagnosing abnormalities such as basophilic leukemia.

A variety of protocols for the conduct of immunoassays, using either polyclonal or monoclonal antibodies specific for BGPs, known in the art and include competitive binding assays and immunoradiometric assays. A two-site monoclonal-based immunoassay utilizing monoclonal antibodies reactive to two noninterfering epitopes on a specific BGP is preferred, but a competitive binding assay can also be employed. These assays are described in the following publications, hereby incorporated by reference: Maddox, D. E. et al, *J Exp Med* (1983) 158:1211; Gleich, G. J. et al, *J Lab Clin Med* (1971) 77:690; Gleich, G. J. et al, *J Allergy Clin Immun* (1974) 53:158; Gleich, G. J. et al, *J Allergy Clin Immun* (1977) 60:188; Dunnette, S. L. et al, *J Immunol* (1977) 119:1727; Wassom, D. L. et al, *J Clin Invest* (1981) 67:651.

Immunoassay procedures are utilized to measure several major parameters in immunopathologic and prepathologic conditions which are characterized by BGP abnormalities—e.g. the increased or decreased production of BGPs by basophils, the aberrant production of BGPs by cells other than basophils, and the change in intracellular or extracellular distribution of BGPs during the genesis of disease. In order to determine the normal distribution of BGP in leukocytes, peripheral blood mononuclear cells from normal individuals are prepared and analyzed as described by Ackerman et al for the localization of eosinophil granules MBP and Charcot-Leyden crystal protein to human basophils. (*J Exp Med* (1983) 158:946; *J Exp Med* (1982) 155:1597). To determine the quantity of BGPs in basophils, freeze-thawed detergent extracts of cell suspensions enriched for basophils are analyzed by immunoassay, and the slope of the binding curves are then compared to comparable binding curves generated by the purified protein.

I. Pharmaceutical Compositions

BGPs are also useful to remedy deficiencies in these proteins or to amplify immune-responses which are stimulated by these proteins. BGPs can be administered to subjects exhibiting such conditions using standard formulations such as those set forth in *Remington's Pharmaceutical Sciences*, Mack Publishing Co., Easton Pa., Latest Ed.

Thus the present invention also provides compositions containing an effective amount of compounds of the present invention, including the nontoxic addition of salts, amides and esters thereof, which may alone serve to provide the above-recited therapeutic benefits. Such compositions can also be provided together with physiologically tolerable liquid, gel or solid diluents, adjuvants and excipients.

These compounds and compositions can be administered to mammals for veterinary use, such as with domestic animals, and clinical use in humans in a manner similar to other therapeutic agents. In general, the dosage required for therapeutic efficacy will range from about 0.01 to 10,000 mcg/kg, more usually 0.1 to 1000 mcg/kg of the host body weight. Alternatively, dosages within these ranges can be administered by constant infusion over an extended period of time, usually exceeding 24 hours, until the desired therapeutic benefits have been obtained.

Typically, such compositions are prepared as injectibles, either as liquid solutions or suspensions; solid forms suitable for solution in, or suspended in, liquid prior to injection may also be prepared. The preparation may also be emulsified. The active ingredient is often mixed with diluents or excipients which are physiologically tolerable and compatible with the active ingredient. Suitable diluents or excipients are, for example, water, saline, dextrose, glycerol, or the like, and combinations thereof. In addition, if desired, the compositions may contain minor amounts of auxiliary substances such as wetting or emulsifying agents, stabilizing or pH-buffering agents, and the like.

The compositions are conventionally administered parenterally, by injection, for example, either subcutaneously or intravenously. Additional formulations which are suitable for other modes of administration include suppositories, intranasal aerosols, and in some cases, oral formulations. For suppositories, traditional binders and excipients may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%–95% of active ingredient, preferably 25%–70%.

The peptide compounds may be formulated into the compositions as neutral or salt forms. Pharmaceutically acceptable nontoxic salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Based on the above, it can be seen that the core of the present invention relates to the novel proteins which are present in the cytoplasmic granules of human basophils, including a subset of those basophil granule proteins which are disclosed and described herein. In addition, the proteins can be applied to various procedures for the diagnosis of diseases related to the abnormal (e.g., over or under) expression of the protein. The proteins can be formulated into pharmaceutical compositions of various types and used for various types of treatments. In addition, the genetic material which encodes the proteins is useful in producing the proteins. The genetic material can be placed in plasmids and the plasmids used to transfect hosts each of which are part of the present invention. The proteins can be used to produce monoclonal and polyclonal antibodies and these antibodies can be used in detection assays of the type described above.

EXAMPLES

The following examples are put forth so as to provide those of ordinary skill in the art with a complete disclosure and description of how to make the proteins of the invention and are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts are parts by weight, molecule weight is weight average of molecular weight, temperature is in degrees Centigrade, and pressure is at or near atmospheric.

The following procedures are used to purify human basophils, isolate the basophil granules, extract basophil granule proteins, fractionate and purify those proteins and determine their N-terminal amino acid sequence.

Preparation of Purified Human Basophil Granules

A patient with a form of chronic myelogenous leukemia (basophil leukemia with leukocyte counts over $10^5$ cells/μl and 78% basophils) underwent two treatments of cytophoresis from which $1.5 \times 10^{11}$ basophils were recovered. The basophils were purified by centrifugation over a cushion of Ficoll-Hypaque from which 95% were recovered from the interface with greater than 90% purity.

Subsequently, these basophils were lysed using modifications of the procedures described by Dvorak et al. Purified basophils were washed with PBS and erythrocytes were lysed by exposure to Tris-ammonium chloride for 5 minutes. The cell suspension was centrifuged at 400× g, washed with Hank's BSS-EDTA and suspended in cold 0.25M sucrose containing DNAase and heparin using a volume of 15 ml for $8 \times 10^8$ basophils. The cell suspension was centrifuged at 400× g for 10 minutes and the sediment was again suspended in 0.25M sucrose containing DNAase (2mg/15ml solution). After 1–2 minutes, heparin (20 IU) dissolved in 2ml 0.24M sucrose was added and the preparation was subjected to a shearing force by repeated passage (15 times) through a 20 gauge needle. The suspension was centrifuged at 400× g to remove intact cells and granules were purified by centrifugation through a cushion of 40% sucrose. The granules were resuspended and stored in 30 aliquots at −70° C.

EXAMPLE 1

Extraction of Basophil Granule Proteins

Four consecutive freeze/thaw cycles were carried out on a single aliquot of purified basophil granules in order to lyse the granules. Proteins were extracted at 4° C by addition of 1 ml of 50 mM sodium borate pH 9.0 to the lysed granules. The extraction mix was vortexed frequently over a 1 hour period to aid extraction. The insoluble material was removed by centrifugation for 15 minutes at 20000× g, and the soluble extract was taken for chromatographic fractionation.

Reverse Phase HPLC

The borate extract was acidified by adjustment to 0.05–0.1% trifluoroacetic acid and was fractionated by reverse phase chromatography on a Brownlee BU300 column (2.1 mm×30 mm) eluted with a 0–70% gradient of acetonitrile in 0.1% trifluoroacetic acid. Fractions judged to be appropriate for analysis were concentrated in a SpeedVac concentrator and sequenced by automated Edman degradation on the ABI 477 Protein Sequenator.

The results are shown in FIG. 1 and described as follows:

Analyses of basophil granule extracts by HPLC chromatogram. Basophil granules were solubilized in 0.05M borate buffer, pH 9, and separated by reverse phase HPLC using a Brownlee BU-300 C4 column. The mobile phase was 0.1% trifluororacetic acid (TFA) containing 0–70% acetonitrile. The % B (0.1% TFA and 70% acetonitrile) is indicated on the graph. The fractions are indicated on the abscissa. The ordinate shows absorbance at 214 nm.
TABLE 1. N-terminal amino acid sequences of proteins purified from basophil granule extracts. "X" represents an unidentified residue.

Each of the sequences listed in Examples 1–3 is given a number designation at the left referred to as the "Fraction No." which is provided only as a matter of reference convenience.
Fraction No.
9—Asp-Ile-Gly-Pro-Asp-Gln-His-Thr-Ser-Arg-Pro-Trp-Gly-Gln-Thr (SEQ ID NO: 1)
11—Asp-Val-Lys-Lys-Asp-Met-Glu-Val-Ser-Cys-Pro-Asp-Gly-Tyr-Thr (SEQ ID NO: 2)
12—Val-Met-X-Pro-Asp-Ala-Arg-Ser-X-Arg-Pro-Asp-Gly-X-Thr (SEQ ID NO: 3)
15—Ala-Ile-Tyr-X-Arg-Ile-Pro-X-X-Ile-Ala-Gly-Glu-Phe-Arg-Tyr-Gly-Thr-Val-Tyr-Tyr-Gln-Gly-Ser-Leu (SEQ ID NO: 4)
20—Asp-Ile-Pro-Glu-Val-X-Val-X-Leu-Ala-Ala-Asp-Glu-Ser-Leu-Ala-Pro-Lys (SEQ ID NO: 5)
30—Tyr-Pro-Gln-Leu-Ala-Ile-Asn (SEQ ID NO: 6)
42—Ser-Ile-Gly-Phe-Val-Glu-Val-X-Leu-Val-Leu (SEQ ID NO: 7)

EXAMPLE 2

Extraction of Basophil Granule Proteins

A cocktail of protease inhibitors was prepared containing diisopropylfluorophosphate, ethylenediaminetetraacetic acid and pepstatin A, and 0.50 ml of the mix was added to each of 2 aliquots of frozen granules. Four consecutive freeze/thaw cycles were carried out in order to lyse the granules. Proteins were extracted at 4° C. by addition of 3 ml of 50 mM sodium borate pH 9.0 to the pooled lysed granules. The extraction mix was vortexed occasionally over 1 hour to aid extraction. The insoluble material was removed by centrifugation for 15 minutes at 20000×g, and the soluble extract was taken for chromatographic fractionation.

Size Exclusion HPLC

Borate extract (4 ml) was concentrated to 0.6 ml and the pH was adjusted to neutral pH with 0.5M $NaH_2PO_4$. The neutralized extract was fractionated by size exclusion chromatography on a Bio-Sil TSK 250 HPLC column (7.5 mm×600 mm). The $A_{280}$ was monitored and the fractions containing proteins were combined into 7 separate pools based on silver staining of Laemmli SDS polyacrylamide gels.

Reverse Phase HPLC

Pools of fractions from size exclusion HPLC were acidified by adjustment to 0.05–0.1% trifluoroacetic acid and each pool was separately fractionated further by reverse phase chromatography on a Brownlee BU300 column (2.1 mm×30 mm) eluted with a 0–70% gradient of acetonitrile in 0.1% trifluoroacetic acid. Fractions judged to be appropriate for analysis were concentrated in a SpeedVAc and sequenced by automated Edman degradation on the ABI 477 Protein Sequenator.

The following sequences were obtained:
1.18  Ala-Cys-Tyr-Cys-Arg-Ile-Pro-Ala-Cys-Ile-Ala-Gly-Glu-Arg-Arg-Tyr-Thr-Cys-Ile (SEQ ID NO: 8)
2.17b Ala-Pro-Ala-Leu-Thr-Ile-Ser-Asn-Gln (SEQ ID NO: 9)
4.10a  Asp-Ile-Gly-Pro-Asp-Gln-His-Thr-Ser-$X_1$-Pro-$X$2-Gly-Gln-Thr-Arg-X-Pro-Gln-Leu-Thr-Gly-Gly-Glu-Ala-X-Val (SEQ ID NO: 10)
where $X_1$ is Ser or Arg and $X_2$ is Val or Trp
4.10b Arg-Asp-Val-Pro-Pro-Asp-X-Val-Val-Ser-X-Pro-Ser-Ser-Asp-Thr (SEQ ID NO: 11)
4.12a  Gly-Asp-Val-Lys-X-Asp-Met-Glu-Val-Ser-X-Pro-Asp-Gly-Tyr-Thr-X-X-Arg-Leu-Gln-Ser-Gly-Ala (SEQ ID NO: 12)
4.12b  Asp-Val-Lys-X-Asp-Met-Glu-Val-Ser-X-Pro-Asp-Gly-Tyr-Thr-X-X-Arg-Leu-Gln-Ser-Gly-Ala (SEQ ID NO: 13)
4.38  Gly-Pro-Pro-Thr-Phe-Asn-Lys-Ile-Thr-Pro-Asn-Asp-Ala-Asp-Phe (SEQ ID NO: 14)

It is pointed out that the above-listed sequence 1.18 is homologous to a family of peptides previously described (Selsted, M. E., Harwig, S. L., Ganz, T., Schilling, J. W., and Lehrer, R. I. (1985) J. Clin. Invest. 76,1436.), but differs from them by virtue of a deletion of Gly found in position 17 of those peptides.

The above-listed sequence 4.12 is nearly identical to the sequence BGP 11 of U.S. parent application Ser. No. 07/551, 263 filed Jul. 10, 1990, which is in turn very similar or identical to granulin A described by Bateman et al. (Bateman, A., Belcourt, D., Bennett, H., Lazure, C. and Solomon, S. (1990) Biochem. Biophys. Res. Comm. 173, 1161), and bears sequence similarity to rat peptides termed epithelins, particularly epithelin 1, described by Shoyab et al. (Shoyab, M., McDonald, V. L., Byles, C., Todaro, G. J. and Plowman, G. D. (1990) Proc. Nat. Acad. Sci. 87, 7912).

Other members of a family of human and rat granulins/epithelins have been described (Bhandari, V., Palfree, R. G. E. and Bateman, A. (1992) Proc. Nat. Acad. Sci. 89, 1715; Plowman, G. D., Green, J. M., Neubauer, M. G., Buckley, S. D., McDonald, V. L., Todaro, G. J. and Shoyab, M. (1992) J. Biol. Chem. 267, 13073.) Except for a Gly in position 1, the peptide of sequence 4.12 may be identical to peptide 11 of parent application Ser. No. 07/551,263.

The above-listed 4.38 is homologous to human α1-antitrypsin (Long, G. L., Chandra, T., Woo, S. L. C., Davie, E. W. and Kurachi, K. (1984) Biochemistry, 23, 4828) and may represent an allelic variant of α1-antitrypsin or may represent another member of a family of related molecules, the serpins, of which α1-antitrypsin is one.

EXAMPLE 3

Extraction of Basophil Granule Proteins

A cocktail of protease inhibitors was prepared containing diisopropylfluorophosphate, ethylenediaminetetraacetic acid and pepstatin A, and 0.25 ml of the mix was added to each of 10 aliquots of frozen granules. Four consecutive freeze/thaw cycles were carried out in order to lyse the granules. Proteins were extracted at 4° C. by addition of 5 ml of 50 mM sodium borate pH 9.0 to the pooled lysed granules. The extraction mix was vortexed occasionally over a 1 hour period to aid extraction. The insoluble material was removed by centrifugation for 15 minutes at 20000×g, and the soluble extract was taken for chromatographic fractionation.

Size Exclusion HPLC

Borate extract (7.2 ml) was concentrated to 1.6 ml and was adjusted to neutral pH with 0.5M $NaH_2PO_4$. The neutralized extract was fractionated by size exclusion chromatography in 3 identical runs on a Bio-Sil TSK 125 HPLC column (7.5 mm×600 mm). The $A_{280}$ was monitored and the fractions containing proteins were combined into 4 separate pools based on silver staining of Laemmli SDS polyacrylamide gels.

Reverse Phase HPLC

Pools of fractions from size exclusion HPLC were acidified by adjustment to 0.05–0.1% trifluoroacetic acid and each pool was separately fractionated further by reverse phase chromatography on a Vydac C4 column (4.6 mm×25 cm) eluted with a 0–100% gradient of acetonitrile in 0.1% trifluoroacetic acid. Fractions judged to be appropriate for analysis were concentrated in a SpeedVac and sequenced by automated Edman degradation on the ABI 477 Protein Sequenator.

Proteins in some fractions were further fractionated by an additional reverse phase HPLC step performed as described in Example 2. Proteins present in other reverse phase fractions were prepared for sequencing of component proteins by Laemmli SDS polyacrylamide gel electrophoresis followed by electrophoretic transfer (2 h at 500 mA in 10 mM CAPS ph 11.0, 10% methanol, 0.05% SDS) of proteins from the gel onto a polyvinylidinedifluoride membrane (ProBlott, ABI). Such electroblotted bands were excised from the membrane and loaded directly onto the ABI 477 Protein Sequenator.

The following sequences were obtained:

Ala-Ile-Gln-Cys-Pro-$\underline{X}_3$-Ser-Gln-Phe-$\underline{X}_4$-$\underline{X}_5$-Pro-$X_6$-Phe-Leu-Ala-Thr-Gly-Val-Met (SEQ ID NO: 15)

where $\underline{X}_3$ is Leu or Asp, $\underline{X}_4$ is Met or Glu, $\underline{X}_5$ is Lys, Ile, or Cys, and $X_6$ is Pro or Leu.

26 Asp-Ile-Pro-Glu-Val-Cys-Phe-Asn (SEQ ID NO: 16)

29 Asp-Pro-Gly-Glu-Val-Lys-Ala-Leu-Pro-Met-Gln (SEQ ID NO: 17)

29 Lys-Pro-Gln-Met-Phe-Thr-Ile-X-Gln-Asn-X-Ala-Thr-Trp-Met (SEQ ID NO: 18)

31 Lys-Ile-Gly-Gly-Phe-Glu-Val-Thr-Asp-Val-Phe-Ala-Pro-Val-Met-Ala (SEQ ID NO: 19)

31rp Ile-Leu-Gly-Val-Phe-X-Val-Glu-Gln-X-Phe-Ser-Phe-X-Leu (SEQ ID NO: 20)

37 Asp-Pro-Pro-Thr-Phe-Asn-Lys-Ile-Thr-pro-Asn-Leu-Leu-Glu-Phe-Ala-Asp-Gly-Leu-Tyr-Lys-Gln-Glu (SEQ ID NO: 21)

26bb1 Ser-Glu-Leu-Thr-Lys-Met-Asn-Gln-Arg-Ser-Phe (SEQ ID NO: 22)

rp indicates that the sequence was obtained following repurification of Fraction 31 of this example.

bb1 indicates that the sequence was obtained following electroblotting of Fraction 26 of this example.

The above-listed sequence 37 has homology with respect to human α1-antitrypsin (Long, G. L., Chandra, T., Woo, S. L. C., Davie, E. W. and Kurachi, K. (1984) Biochemistry, 23,4828) and may represent an allelic variant of α1-antitrypsin or may represent another member of a family of related molecules, the serpins, of which α1-antitrypsin is one.

Each of the 29 remaining vials of basophil cells contains an estimated 200 µg of extractable protein. Individual proteins recovered had yields ranging from 250 pmoles for peak 21 down to 25–50 pmoles for peaks 9 and 37 (FIG. 1). Since 25 pmoles is usually sufficient for sequencing 20 or more residues at the N-terminus, the expenditure of more vials will enable rarer species of proteins to be sequenced and will also enable more residues to be sequenced from all proteins.

The instant invention has been shown and described herein and was considered to be the most practical, and preferred embodiments. It is recognized, however, that departures may be made therefrom which are within the scope of the invention, and that obvious modifications will occur to one skilled in the art upon reading this disclosure.

What is claimed is:
1. An isolated and purified basophil protein (BGP) wherein the BGP has an N-terminal sequence described by a sequence selected from the group consisting of:

Asp-Ile-Gly-Pro-Asp-Gln-His-Thr-Ser-Arg-Pro-Trp-Gly-Gln-Thr (SEQ. ID NO. 1);

Asp-Val-Lys-Lys-Asp-Met-Glu-Val-Ser-Cys-Pro-Asp-Gly-Tyr-Thr (SEQ. ID NO. 2);
Val-Met-X-Pro-Asp-Ala-Arg-Ser-X-Arg-Pro-Asp-Gly-X-Thr (SEQ. ID NO. 3);
Ala-Ile-Tyr-X-Arg-Ile-Pro-X-X-Ile-Ala-Gly-Glu-Phe-Arg-Tyr-Gly-Thr-Val-Tyr-Tyr-Gln-Gly-Ser-Leu (SEQ. ID NO. 4);
Asp-Ile-Pro-Glu-Val-X-Val-X-Leu-Ala-Ala-Asp-Glu-Ser-Leu-Ala-Pro-Lys (SEQ. ID NO. 5);
Tyr-Pro-Gln-Leu-Ala-Ile-Asn (SEQ. ID NO. 6);
Ser-Ile-Gly-Phe-Val-Glu-Val-X-Leu-Val-Leu (SEQ. ID NO. 7);
Ala-Cys-Tyr-Cys-Arg-Ile-Pro-Ala-Cys-Ile-Ala-Gly-Glu-Arg-Arg-Tyr-Thr-Cys-Ile (SEQ. ID NO. 8);
Ala-Pro-Ala-Leu-Thr-Ile-Ser-Asn-Gln (SEQ. ID NO. 9);
Asp-Ile-Gly-Pro-Asp-Gln-His-Thr-Ser-$X_1$-Pro-$X_2$-Gly-Gln-Thr-Arg-X-Pro-Gln-Leu-Thr-Gly-Gly-Glu-Ala-X-Val (SEQ. ID NO. 10);
Arg-Asp-Val-Pro-Pro-Asp-X-Val-Val-Ser-X-Pro-Ser-Ser-Asp-Thr (SEQ. ID NO. 11);
Gly-Pro-Pro-Thr-Phe-Asn-Lys-Ile-Thr-Pro-Asn-Asp-Ala-Asp-Phe (SEQ. ID NO. 14);
Ala-Ile-Gln-Cys-Pro-$X_3$-Ser-Gln-Phe-$X_4$-$X_5$-Pro-$X_6$-Phe-Leu-Ala-Thr-Gly-Val-Met (SEQ. ID NO. 15);
Asp-Ile-Pro-Glu-Val-Cys-Phe-Asn (SEQ. ID NO. 16);
Asp-Pro-Gly-Glu-Val-Lys-Ala-Leu-Pro-Met-Gln (SEQ. ID NO. 17);
Lys-Pro-Gln-Met-Phe-Thr-Ile-X-Gln-Asn-X-Ala-Thr-Trp-Met (SEQ. ID NO. 18);
Lys-Ile-Gly-Gly-Phe-Glu-Val-Thr-Asp-Val-Phe-Ala-Pro-Val-Met-Ala (SEQ. ID NO. 19);
Ile-Leu-Gly-Val-Phe-X-Val-Glu-Gln-X-Phe-Ser-Phe-X-Leu (SEQ. ID NO. 20);
Asp-Pro-Pro-Thr-Phe-Asn-Lys-Ile-Thr-Pro-Asn-Leu-Leu-Glu-Phe-Ala-Asp-Gly-Leu-Tyr-Lys-Gln-Glu (SEQ. ID NO. 21); and
Ser-Glu-Leu-Thr-Lys-Met-Asn-Gln-Arg-Ser-Phe (SEQ. ID NO. 22);

where each X, $X_1$, $X_2$, $X_3$, $X_4$, $X_5$ and $X_6$ independently represents a variable amino acid residue.

2. The BGP of claim 1, wherein $X_1$ is Ser or Arg and $X_2$ is Val or Trp.

3. The BGP of claim 1, wherein $X_3$ is Leu or Asp, $X_4$ is Met or Glu, $X_5$ is Lys, Ile or Cys, and $X_6$ is Pro or Leu.

4. A pharmaceutical composition which comprises the BGP of claim 1 as an active ingredient in admixture with a pharmaceutical excipient.

* * * * *